United States Patent

Asano et al.

[11] Patent Number: 5,948,961
[45] Date of Patent: Sep. 7, 1999

[54] APPARATUS AND METHOD FOR DETECTING FRICTION CHARACTERISTICS

[75] Inventors: Katsuhiro Asano; Masaru Sugai, both of Aichi-ken, Japan

[73] Assignee: Kabushiki Kaisha Toyota Chuo Kenkyusho, Aichi-ken, Japan

[21] Appl. No.: 08/659,010

[22] Filed: Jun. 4, 1996

[30] Foreign Application Priority Data

Jun. 5, 1995 [JP] Japan ................................. 7-138307

[51] Int. Cl.⁶ .................................................. G01N 3/56
[52] U.S. Cl. ............................................................. 73/9
[58] Field of Search ............................................ 73/9, 10

[56] References Cited

U.S. PATENT DOCUMENTS 5,107,448  4/1992  Nash .
5,588,721  12/1996  Asano et al. .

FOREIGN PATENT DOCUMENTS 0 252 384   1/1988   European Pat. Off. .
0 294 803   12/1988  European Pat. Off. .
0 449 118   10/1991  European Pat. Off. .
0 469 246   2/1992   European Pat. Off. .
0 699 568   3/1996   European Pat. Off. .
4-84652     3/1992   Japan .

OTHER PUBLICATIONS

Patent Abstracts of Japan, vol. 016, No. 302 (M–1275), Jul. 3, 1992, JP 04 084652, Mar. 17, 1992.

*Primary Examiner*—Robert Raevis
*Attorney, Agent, or Firm*—Oblon, Spivak, McCLelland, Maier & Neustadt, P.C.

[57] ABSTRACT

An apparatus and method for detecting friction characteristics are disclosed, in which a wheel resonant system includes a vehicle body, a road surface and at least a wheel. A braking force control system exerts a braking force on the wheel. A resonant component detector determines a resonant gain providing the ratio between the amplitude of predetermined frequency component of the braking force and that of the wheel velocity and detects the ratio of the resonant gain to a present reference gain, a deviation calculator calculates the deviation between this ratio and unity, a PI controller controls the braking force control system in such a manner that the deviation coincides with zero, and a friction characteristics detector detects the friction characteristics on the basis of the braking force. When the friction force is made to approach a peak value by increasing the braking force, the resonant characteristics undergo a change thereby to reduce the resonant gain. By controlling the braking force in such a manner that the deviation coincides with zero, therefore, the friction characteristics are held at a peak value. This braking force reflects the friction characteristics, and therefore the friction characteristics between the road surface and the wheel can be accurately detected according to the relative magnitude of the braking force.

16 Claims, 15 Drawing Sheets

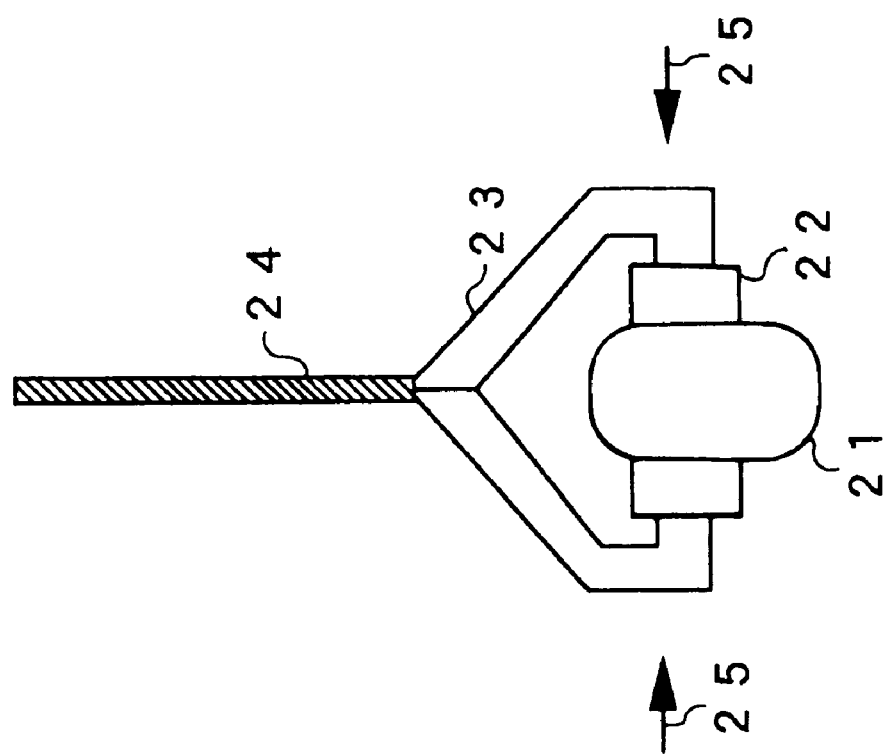
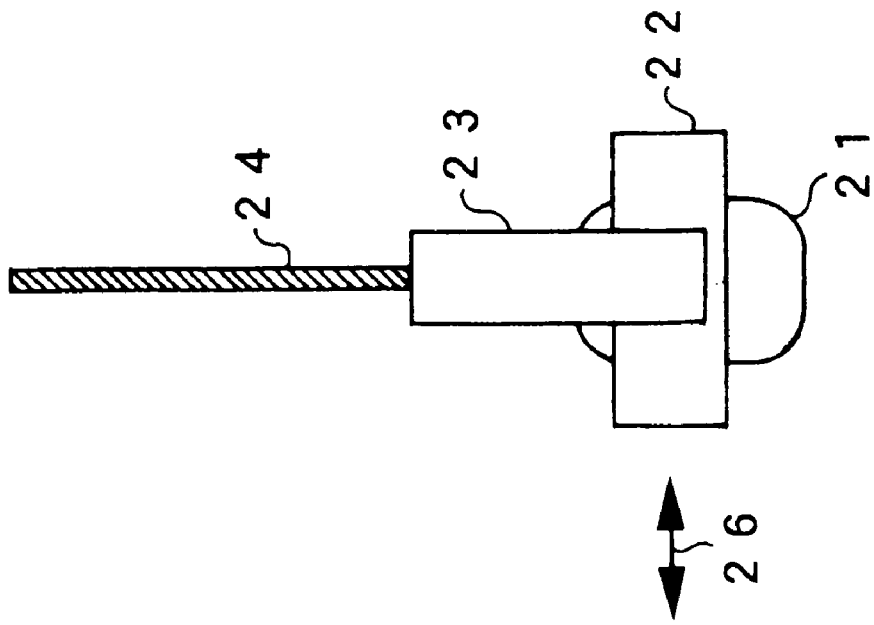

APPARATUS AND METHOD FOR DETECTING FRICTION CHARACTERISTICS

BACKGROUND OF THE INVENTION

1. Field of the Invention

The present invention relates to an apparatus and method for detecting the friction characteristics, or more in particular to a friction characteristics detecting apparatus for controlling the wheel regulating force to a value in the vicinity of the peak friction force on the basis of the resonant characteristics of a wheel resonant system including the road surface and at least a wheel and detecting the friction characteristics on the basis of the regulating force thus controlled.

2. Description of the Related Art

Some techniques for measuring the friction force or the friction coefficient and techniques for controlling the friction force by detecting the friction characteristics are described below.

In a model shown in FIG. 7, the maximum friction force $F_{max}$ generated between an object 1 of mass M and a surface to be measured 2 is given as $$F_{max} = \mu_{stat} \cdot W$$

where W is a load (=Mg, where g is the acceleration of gravity) and $\mu_{stat}$ is the static friction coefficient. In the case where a force $F_{ext}$ applied from an external source is equal to or below the maximum friction force $F_{max}$, the static state is retained. Once the external force $F_{ext}$ exceeds the maximum friction force $F_{max}$, however, the object abruptly begins to slip. The friction force $F_{trans}$ involved is expressed as $$F_{trans} = \mu_{trans} \cdot W$$

where $\mu_{trans}$ is the dynamic friction coefficient.

In this way, the object remains totally unchanged until the external force $F_{ext}$ exceeds the maximum friction force $F_{max}$, and the characteristics undergo a great change immediately upon exceeding the maximum friction force. It is therefore very difficult to determine whether the object is just about to slip or not.

In conventional systems for measuring the friction force, an object is caused to slip by applying an external force thereto in advance and the maximum friction force $F_{max}$ involved is measured. Further, the maximum friction force $F_{max}$ is divided by the weight of the apparatus thereby to measure the static friction coefficient $\mu_{stat}$.

Also, in the field of casting industry, there is a technique for measuring the friction force, wherein a die for continuous casting is fixedly supported on a vibrating table and coupled to a vibration source through a vibrating beam. The vibrating beam is oscillated about a supporting point by the operation of the vibration source, and the friction force exerted between the die and the cast piece is measured when drawing the cast piece while vibrating the die. These techniques take advantage of the fact that the friction force between the die and the cast piece affects the load of the vibration source, and the characteristics of the die vibrating system are expressed by a transfer function, so that the friction force between the die and the cast piece is measured on the basis of the transfer function. These techniques for measuring the friction force in the field of casting engineering include the one disclosed in Japanese Patent Application Laid-Open (JP-A) No.4-84652 as a technique securing an improved calculation speed and accuracy of calculation.

In the technique disclosed in Japanese Patent Application Laid-Open (JP-A) No.4-84652, the friction force exerted between a die and a cast piece when drawing a cast piece from the die under vibration is calculated on the basis of the oscillation torque exerted on the die under vibration and the displacement generated in the die by the vibration according to a state space model obtained by formulating the portion nearer to the die than the supporting point of the vibrating beam by the mode separation method. In order to accurately determine the oscillation torque acting on the die, the exciting force generated by a vibration source such as a vibrating cylinder and the stress generated in the vibrating beam at a portion nearer to the vibration source than the supporting point of the vibrating beam are detected, and the exciting force thus detected is corrected by the stress generated in the vibrating beam, thereby calculating the oscillation torque. In this way, according to this technique, a high-speed calculation is accomplished by modeling the portion between the supporting point of the vibrating beam and the die to be vibrated in a simplified way as a flexible beam for vibrating a concentrated mass including a vibrating table and a die by the oscillation torque exerted on the supporting point. Further, in calculating the oscillation torque, the exciting force is corrected by the stress of the vibrating beam, thereby making it possible to measure the friction force accurately.

In the field of automotive control engineering, a technique for measuring the friction coefficient between the wheels and the road surface and controlling the operation on the basis of the friction coefficient is presented by an electronically-controlled power steering apparatus disclosed in Japanese Patent Application Laid-Open (JP-A) No.4-230472.

The method for measuring the friction coefficient disclosed in Japanese Patent Application Laid-Open (JP-A) No.4-230472 is such that a vibration signal is applied to a solenoid valve from a controller, whereby the rear wheels are manipulated periodically at a steering angle equivalent to +/-1 mm and a frequency of 2 Hz, and the reaction force against the self-aligning torque and the cornering force generated in the rear wheels by this periodic steering operation are detected by a reaction force sensor such as a load cell. The cornering power and the self-aligning power are calculated on the basis of the reaction force thus detected, and the road surface friction coefficient is measured from the calculation result on the basis of the relation between these powers and the road surface friction coefficient.

Also, an anti-lock brake control apparatus is known as a technique for preventing the wheels from locking and slipping even under a suddenly braked condition by estimating the friction characteristics between the road surface and the wheel and controlling the braking force in such a manner that the contact surface reaches the stage just about to slip.

Suppose that the braking force is progressively applied when the vehicle is running at a predetermined velocity. A slip occurs between the wheel and the road surface. The friction coefficient $\mu$ between the wheel and the road surface, however, is known to change as shown in FIG. 9 with respect to the slip ratio S expressed by equation (1) below.

$$S = (v_{v^*} - v_w)/v_{v^*} \tag{1}$$

where $v_{v^*}$ is the velocity of an actual vehicle body, and $v_w$ is the wheel velocity.

With this $\mu$–S characteristic, the friction coefficient $\mu$ assumes a peak value for a predetermined slip ratio (region A2 in FIG. 9).

In the conventional anti-lock brake control apparatus, therefore, the slip ratio is detected from the vehicle body velocity and the wheel velocity, and the braking force is controlled in such a manner as to secure a slip ratio associated with the peak value of the friction coefficient $\mu$.

With the above-mentioned conventional friction force detecting apparatus, however, in the event that the slip is not allowed or the friction coefficient undergoes a change, it is very difficult to detect in real time which state the friction characteristics are in at present.

The friction force measuring apparatus disclosed in Japanese Patent Application Laid-Open (JP-A) No.4-84652 assumes a linear model of a die approximated by the concentrated mass under vibration by a oscillation torque and calculates the friction force affecting the die vibration on the basis of only the displacement of the die and the oscillation torque. The problem therefore is that the measurement is liable to be affected by noises, etc. Under the conditions failing to satisfy the foregoing assumption, accurate measurement of the friction force is impossible with this model, and therefore the range of application is very limited. Even if a model meeting the conditions of assumption can be constructed, complicated calculations are often required depending on the model. In such a case, a new problem is posed that the friction force cannot be calculated in real time.

Also, in the method for measuring the coefficient of friction disclosed in Japanese Patent Application Laid-Open (JP-A) No.4-230472, the cornering force and the like are required to be generated by periodically steering the wheels and the reaction of the wheels against the cornering force must be detected. This poses the problem of a complicated measuring system. Further, since the relation between the cornering power or the like and the road surface coefficient of friction is assumed with a predetermined model, the system easily succumbs to noises.

With the conventional anti-lock brake control apparatus, the friction coefficient $\mu$ between the tire of a running vehicle and the road surface undergoes a constant change and considerable disturbance and noises are generated while the vehicle is running. The slip ratio associated with the maximum friction coefficient $\mu$, therefore, also undergoes a change, thereby making it very difficult to accomplish a proper brake control.

The object of the present invention, which has been developed in order to obviate the above-mentioned problems of the prior art, is to provide a friction characteristics detecting apparatus having a simple configuration for a wide range of applications, in which the friction characteristics are not detected only on the basis of the displacement response or the vibration characteristics or the like for an assumed model depending to a large measure on the system configuration and conditions, but the braking force applied to the wheels is controlled in such a manner that the friction force assumes a peak value on the basis of the resonant gain quickly reflecting the friction characteristics between the wheel and the road surface, and the friction characteristics are detected based on the particular braking force. Thus it is possible to accurately detect the friction characteristics even in the case where noises are considerable and the fiction characteristics are constantly undergoing a change.

SUMMARY OF THE INVENTION

According to a first aspect of the present invention, there is provided an apparatus for detecting friction characteristics comprising: a vibrating system including an element on one side of a contact surface generating a friction force, a spring element connected to said element and adapted to be displaced in the direction substantially parallel to said contact surface and an inertial member connected to the other end of said spring element; exciting force generating means for generating an exciting force containing selected one of the resonant frequency of said vibrating system and the frequency component in the vicinity of said resonant frequency and exciting said vibrating system by said exciting force; vibration response detecting means for detecting the quantity of state of the vibration response of said vibrating system excited by said exciting force generating means; resonant characteristics calculating means for calculating the resonant characteristics of said vibrating system on the basis of the quantity of state of the exciting force generated by said exciting force generating means and the quantity of state of the vibration response detected by said vibration response detecting means; and friction characteristics calculation means for calculating the friction characteristics of the contact surface on the basis of the resonant characteristics calculated by said resonant characteristics calculating means.

According to a second aspect of the present invention, there is provided an apparatus for detecting friction characteristics comprising: a vibrating system including an element on one side of a contact surface generating a friction force, a spring element connected to said element and adapted to be displaced in the direction substantially parallel to said contact surface and an inertial member connected to the other end of said spring element, said vibrating system being excited by an external force; external force detecting means for detecting the quantity of state of said external force; vibration response detecting means for detecting the quantity of state of the vibration response of said vibrating system excited by said external force; resonant characteristics calculating means for calculating the resonant characteristics of said vibrating system on the basis of the quantity of state of said external force detected by said external force detecting means and the quantity of state of the vibration response detected by said vibration response detecting means; and friction characteristics calculating means for calculating the friction characteristics of the contact surface on the basis of the resonant characteristics calculated by said resonant characteristics calculating means.

According to a third aspect of the present invention, there is provided an apparatus for detecting friction characteristics comprising: a vibrating system including an element on one side of a contact surface generating a friction force, a spring element connected to said element and adapted to be displaced in the direction substantially parallel to said contact surface and an inertial member connected to the other end of said spring element; exciting means for exciting said vibrating system in the direction of generation of the friction force by the exciting force containing selected one of the resonant frequency of said vibrating system and the frequency component in the vicinity of said resonant frequency; vibration response detecting means for detecting the quantity of state of the vibration response of said vibrating system excited by said exciting means; resonant characteristics calculating means for calculating the resonant characteristics of said vibrating system on the basis of the quantity of state of the exciting force generated by said exciting means and the quantity of state of the vibration response detected by said vibration response detecting means; operating force generating means for generating and exerting the operating force on said contact surface; and maximum friction force control means for controlling said operating force on the basis of the resonant characteristics calculated by said resonant characteristics calculating means in such a manner that said contact surface assumes a state just about to slip.

According to a fourth aspect of the present invention, there is provided an apparatus for detecting friction characteristics comprising: a vibrating system including an element on one side of a contact surface generating a friction force, a spring element connected to said element and adapted to be displaced in the direction substantially parallel to said contact surface and an inertial member connected to the other end of said spring element, said vibrating system being excited by an external force; external force detecting means for detecting the quantity of state of said external force; vibration response detecting means for detecting the quantity of state of the vibration response of said vibrating system excited by said external force; resonant characteristics calculating means for calculating the resonant characteristics of said vibrating system on the basis of the quantity of state of the external force detected by said external force detecting means and the quantity of state of the vibration response detected by said vibration response detecting means; operating force generating means for generating and exerting an operating force on said contact surface; and maximum friction force control means for controlling said operating force on the basis of the resonant characteristics calculated by said resonant characteristics calculating means in such a manner that said contact surface assumes a state just about to slip.

According to a fifth aspect of the present invention, the apparatus according to the third or the fourth aspect further comprising: maximum friction force calculating means for calculating the value of maximum friction force of the contact surface on the basis of the operating force associated with the state of said contact surface just about to slip realized by said maximum friction force control means; and friction coefficient calculating means for calculating the friction coefficient of said contact surface on the basis of the value of the maximum friction force calculated by said maximum friction force calculating means.

In the apparatus of the first aspect, the vibrating system including an element on one side of a contact surface generating the friction force, a spring element connected to the element and adapted to be displaced in the direction substantially parallel to the contact surface and an inertial member connected to the other end of the spring element, is vibrated by the exciting force containing selected one of the resonant frequency of the vibrating system and a frequency component in the vicinity of the resonant frequency. The displacement of the spring element can be set arbitrarily in a preferred direction (including the contact plane) as far as it is substantially parallel to the contact surface. Then, the vibration response detecting means detects the quantity of state of the vibration response of the vibrating system thus excited. This vibration response includes, for example, the acceleration of the inertial member due to the exciting force, and the quantity of state includes, for example, the frequency distribution of the frequency components of acceleration. Next, the resonant characteristics calculating means calculates the resonant characteristics of the vibrating system on the basis of the quantity of state of the exciting force and the quantity of state of the vibration response detected. The friction characteristics calculating means calculates the friction characteristics of the contact surface on the basis of the resonant characteristics calculated. The friction characteristics thus calculated permits quantitative identification and determination whether the contact surface is in the state not slipping, just about to slip or in the slip state. Also, the utilization of the resonant characteristics of the vibrating system leads to the advantage of a high detection sensitivity which is not easily affected by noises such as external disturbances.

In the system of the first aspect, in the case of calculation to determine whether the contact surface is in the friction state just about to slip, the vibrating system is excited at selected one of the resonant frequency thereof with the contact surface not slipping and the frequency in the vicinity of the resonant frequency, for example, the resonant gain of the component excited at the resonant frequency is calculated, and when this resonant gain is reduced below a first reference value, the friction characteristics are associated with the state just about to slip. Also, the vibrating system is excited at the resonant frequency with the contact surface in slip motion, and when the resonant gain of the component vibrating at this frequency is increased beyond a second reference value, determination is made that the contact surface is in the state just about to slip. Further, the vibrating system may alternatively be excited with a exciting force containing the frequency components of at least the above-mentioned two resonant frequencies and the friction characteristics are calculated on the basis of the change in the components of the resonant frequencies.

Also, in the case where an external force having the frequency characteristics like white noise, etc., is constantly applied to the vibrating system, the vibrating system is excited with a resonant characteristic specific to the friction characteristics without applying any exciting force thereto from the exciting force generating means.

In view of this, in the system of the second aspect, the external force detecting means detects the quantity of state of an external force, and the response vibration detecting means detects the quantity of state of the response vibration of the vibrating system with respect to the external force. Next, the resonant characteristics calculating means calculates the resonant characteristics on the basis of the external force detected and the quantity of state of the response vibration. Further, the friction characteristics calculating means calculates the friction characteristics of the contact surface on the basis of the resonant characteristics thus calculated. In this way, in the case where the vibrating system is resonated under an external force, the exciting force generating means can be omitted without, and the apparatus can thereby be configured in simplified fashion.

Also, the principle of detecting the friction characteristics on the basis of the resonant characteristics as described above can be applied to any apparatus controlled to a state in which the contact surface is just about to slip, i.e., in such a manner that the apparatus holds the maximum friction force.

As a consequence, in the system of the third aspect, the exciting force generating means vibrates the vibrating system by a exciting force containing selected one of the resonant frequency of the vibrating system and the frequency component in the vicinity of the resonant frequency. Next, the vibration response detecting means detects the quantity of state of the vibration response of the vibrating system thus excited, and the resonant characteristics calculating means calculates the resonant characteristics of the vibrating system on the basis of the quantity of state of the exciting force and the quantity of state of the vibration response detected. Also, the element on one side of the contact surface is subjected to the operating force by the operating force generating means. This operating force is controlled by the maximum friction force control means in such a manner that the contact surface is in a state just about to slip on the basis of the resonant characteristics calculated. With an apparatus used for gripping, lifting up and moving a load, for example, the force (operating force) for gripping the load is controlled in such a way that the surface in contact with the load is in a frictional state just about to slip. The damage to the load by an unnecessarily large gripping force, therefore, can be avoided. Other specific examples of the operating force other than the gripping force include the exciting force for rotating a wheel or the like and the braking force acting on a wheel or the like. When the braking force is controlled in such a manner that the friction characteristics between the wheel and the road surface is in a state just about to slip, an application can also find in an anti-lock brake control apparatus with equal effect.

In the case where an external force having the frequency characteristics like white noise is constantly applied to a vibrating system as in the second aspect of the invention, the vibrating system is excited with the resonant characteristics specific to the friction characteristics without applying any exciting force from the exciting force generating means.

Hence, according to the fourth aspect, the external force detecting means detects the quantity of state of an external force, and the vibration response detecting means detects the quantity of state of the response vibration of the vibrating system with respect to the external force. Next, the resonant characteristics calculating means calculates the resonant characteristics on the basis of the external force detected and the quantity of state of the vibration response. Also, an operating force is applied by the operating force generating means to the element on one side of the contact surface. This operating force is controlled by the maximum friction force control means on the basis of the resonant characteristics in such a manner that the contact surface is in a state just about to slip. In the case where the vibrating system resonates under an external force in this way, the exciting force generating means can be omitted so that the apparatus can be configured in simplified fashion.

Also, in the case where the operating force is controlled in such a manner that the contact surface is kept in a state just about to slip as in the third or fourth aspect of the invention, the force generated in the contact surface by the operating force is equal to the maximum friction force. As a result, the value of the maximum friction can be calculated on the basis of the operating force. Once the value of the maximum friction comes to be known, therefore, the static friction coefficient can be determined by dividing the maximum friction force by the apparatus weight.

With this fact, in the friction characteristics detecting apparatus according to the fifth aspect of the invention, the maximum friction calculating means calculates the value of the maximum friction of the contact surface on the basis of the operating force associated with the state of the contact surface just about to slip. The friction coefficient calculating means then calculates the static friction coefficient on the basis of the value of the maximum friction force thus calculated. As a result, even in the case of making measurements on the road surface with the coefficient of friction thereof under constant change, the static friction coefficient can be detected continuously with high accuracy.

According to a sixth aspect of the present invention, there is provided an apparatus for detecting friction characteristics comprising: a vehicle wheel resonant system including at least a wheel in contact with a road surface; detecting means for detecting the velocity of said wheel; a braking force control system for exerting a braking force on said wheel for suppressing the rotation of said wheel; resonant characteristics calculating means for calculating the resonant gain providing the ratio of the amplitude value of a predetermined frequency component of said wheel velocity to the amplitude value of a predetermined frequency component of said braking force; control means for controlling said braking force control system in such a manner that the resonant gain calculated by said resonant characteristics calculating means coincides with a present reference gain; and friction characteristics detecting means for detecting the friction characteristics between the road surface and the wheel on the basis of the braking force of said braking force control system in the state where the resonant gain is made to coincide or substantially coincide with the reference gain by said control means.

In the apparatus of the sixth aspect of the invention, the wheel included in the wheel resonant system is rotated while being kept in contact with the road surface, and the braking force control system exerts the braking force on the wheel for suppressing the rotation thereof. The braking pressure, for example, constitutes a force equivalent to the braking force. The detecting means detects the wheel velocity. The resonant characteristics calculating means calculates the resonant gain providing the ratio of the amplitude value of a predetermined frequency component of the wheel velocity to the amplitude value of a predetermined frequency component of the braking force. In the process, the control means controls the braking force control system in such a manner that the resonant gain calculated by the resonant characteristics calculating means coincides with a reference gain set to a sufficiently small value in advance. Suppose, in this case, that the braking force is increased up to about the state where the wheel is locked by the braking force control system. The resonant characteristics undergo a change in the vicinity of the peak value of the braking force of the road surface, so that the resonant gain is decreased. Since the reference gain is set to a sufficiently small value, the braking force retains a value near to the peak under the control of the control means. The relative magnitude of the braking force reflects the friction characteristics between the road surface and the wheel. As a result, the friction characteristics detecting means is capable of detecting the friction characteristics between the road surface and the wheel on the basis of the braking force of the braking force control means in the state where the resonant gain is made to coincide or substantially coincide with the reference gain by the control means.

According to a seventh aspect of the present invention, in the apparatus according to the sixth aspect, the control means includes: dividing means for dividing the resonant gain by said reference gain; deviation calculating means for calculating the deviation between the reciprocal of the quotient obtained by said dividing means and unity; and a controller for controlling said braking force control system in such a manner that the deviation calculated by said deviation calculating means coincides with zero.

According to the seventh aspect, in a friction characteristics detecting apparatus, when the braking force control system is controlled by the control means, the dividing means divides the resonant gain by a reference value preset to a sufficiently small value. Next, the deviation calculating means calculates the deviation between the reciprocal of the quotient obtained by the dividing means and unity. The braking force control system is thus controlled by the controller in such a manner that the deviation (1—ratio between reference gain and resonant gain) obtained by the deviation calculating means coincides with zero.

The controller performs the control operation such that when the ratio between resonant gain and reference gain is larger than unity, it determines that the braking force assumes a value sufficiently small as compared with the peak value of the friction force between the wheel and the road surface. The braking force thus is increased thereby to approach to the peak value. Conversely, with the decrease of the ratio between resonant gain and reference gain below unity, the controller determines that the peak value is being approached and reduces the braking force in such a way as to prevent further increase of the braking force. In this way, the ratio between resonant gain and reference gain is controlled to coincide with unity, whereby the friction characteristics between the road surface and the wheel can be detected from the value of the braking force. The straightforward use of the deviation between unity and the ratio between resonant gain and reference gain is also possible. In such a case, however, when the ratio between resonant gain and reference gain would assume a value smaller than unity, the braking force assumes a value sufficiently near to the peak value, with the probable result that the wheels may be locked in response to a slight change in the braking force. In the case where the reciprocal of the ratio between resonant gain and reference gain is employed as according to the present invention, however, the sensitivity for the deviation increases according as the ratio between resonant gain and reference gain is reduced smaller than unity, i.e., approaches a locked state. Therefore, the braking force can be held at a peak value and the friction characteristics can be detected while avoiding the likelihood of falling in a locked state.

BRIEF DESCRIPTION OF THE DRAWINGS

FIGS. 1A and 1B show an external appearance of a load gripping apparatus according to a first embodiment of the invention, in which FIG. 1A is a front view and FIG. 1B a side view.

FIGS. 3A and 3B show an external appearance of a friction coefficient measuring system according to a second embodiment of the invention, in which FIG. 3A is a front view and FIG. 3B is a side view.

FIGS. 6A and 6B show a modification of a friction coefficient measuring system according to the second embodiment, in which FIG. 6A is a front view and FIG. 6B is a side view.

FIGS. 17A through 17F are graphs showing the result of operation of a friction characteristics detecting apparatus according to an embodiment of the present invention as measured in the case where the peak value of the road surface friction coefficient changes in sinusoidal wave fashion, in which FIG. 17A shows the chronological change of the peak value $\mu$ of the actual road surface friction coefficient as an object of measurement, FIG. 17B the chronological change of the wheel velocity $\omega_w$, FIG. 17C the chronological change of the slip ratio, FIG. 17D the chronological change of the road surface friction coefficient estimated by the friction characteristics detecting apparatus according to this embodiment, FIG. 17E the chronological change of the resonant gain estimated by the friction characteristics detecting apparatus according to this embodiment, and FIG. 17F the chronological change of the braking torque applied to the wheel.

FIGS. 18A through 18F are graphs showing the result of operation of a friction characteristics detecting apparatus according to an embodiment of the invention as measured in the case where the peak value of the road surface friction coefficient changes stepwise, in which FIG. 18A shows the chronological change of the peak value $\mu$ of the actual road surface friction coefficient as an object of measurement, FIG. 18B the chronological change of the wheel velocity $\omega_w$, FIG. 18C the chronological change of the slip ratio, FIG. 18D the chronological change of the road surface friction coefficient estimated by the friction characteristics detecting apparatus according to this embodiment, FIG. 18E the chronological change of the resonant gain estimated by the friction characteristics detecting apparatus according to this embodiment, and FIG. 18F the chronological change of the braking torque acting on the wheels.

DESCRIPTION OF THE PREFERRED EMBODIMENTS

Figure 8:
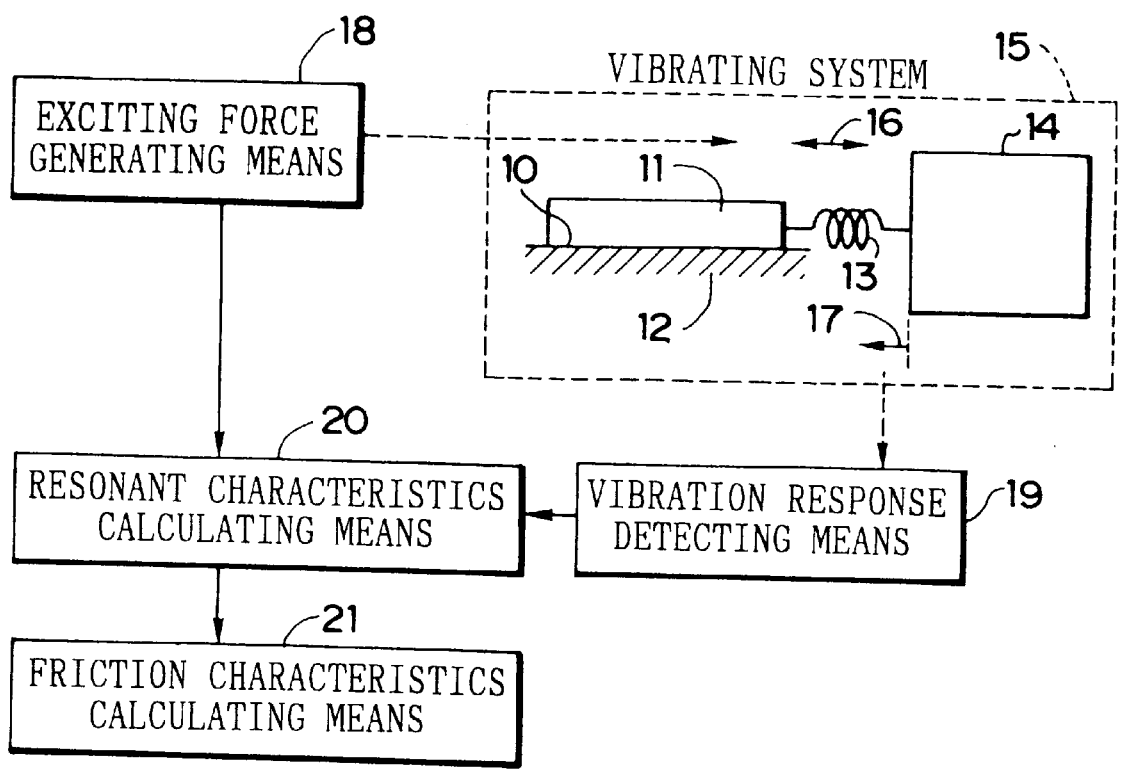
FIG. 8 is a diagram showing an equivalent model of a vibrating system for explaining the principle of detecting the friction characteristics utilizing the resonant characteristics.

First, the principle of the present invention will be explained with reference to a vibrating system 15 shown in FIG. 8 as a model. As shown in FIG. 8, the vibrating system 15 includes an inertial member 11 of mass $M_a$, an inertial member 12 of mass $M_b$ in contact with the inertial member 11 through a contact surface 10, a spring element 13 having a spring constant of K mounted at an end of the inertial member 11, and an inertial member 14 of mass $M_c$ mounted at the other end of the spring element.

The vibrating system 15 is such that the inertial member 12 vibrates in reaction with the inertial member 11 in the case where the friction force generated on the contact surface 10 is not more than the maximum friction force and therefore the contact surface 10 is yet to slip. This vibrating system 15 is therefore equivalent to a double inertial system including the mass $(M_a+M_b)$, a spring of spring constant K and the mass $M_c$. As a result, the resonant frequency $f_1$ for the vibrating system 15 with the friction force not more than the maximum friction force is given as $$f_1 = \text{square root } \{(M_a+M_b+M_c)K/(M_a+M_b)M_c\}/2\pi \quad (2)$$

Also, if the other inertial member 12 has a fixed end, the resonant frequency $f_1$ in equation (2) can be given as $$f_1 = \text{square root } (K/M_c)/2\pi \tag{3}$$

In the state where the friction force exceeds the maximum friction force whereby the contact surface begins to slip, on the other hand, the inertial member 12 cannot follow the vibration of the inertial member 11 and therefore has no effect of the inertia thereof. The vibrating system 15, therefore, becomes equivalent to the double inertial system including mass $M_a$ and mass $M_c$. The resonant frequency $f_2$ of this system is given as $$f_2 = \text{square root } \{(M_a+M_c)K/M_aM_c\}/2\pi \tag{4}$$

Suppose the vibrating system 15 is slightly vibrated by a exciting force 16 at a resonant frequency $f_1$ or a frequency in the vicinity of $f_1$ in the direction parallel to the contact surface 10. As far as the contact surface 10 is not slipping, the resonant frequency $f_1$ of the vibrating system 15 remains $f_1$. In the vibrating system 15, therefore, the frequency component of the frequency $f_1$ is amplified. In other words, the vibrating system 15 enters a resonant state in which the frequency component in the vicinity of the frequency $f_1$ strongly presents itself. By the way, the resonant characteristics of the vibrating system 15 can be represented by the resonant gain as expressed by the ratio between the amplitude of the force 16 and the amplitude of the frequency component of the vibrating system 15, for example. This resonant gain increases in a resonant state and is smaller than in the resonant state when the system is not in resonant state.

When the force in the direction opposite to the friction force approaches the maximum friction force on the contact surface 10 and the contact surface 10 reaches a stage just about to slip, a phase difference begins to develop between the vibration due to the exciting force 16 and the vibration of the inertial members, thereby sharply reducing the resonant gain.

When the contact surface 10 transfers to a state in which it completely slips, the resonant frequency of the vibrating system 15 comes to coincide with $f_2$. The frequency component of the frequency $f_1$ given by the exciting force 16, therefore, is attenuated and the vibrating system 15 ceases to resonate.

Consider the case where the vibrating system 15 is vibrated by the exciting force 16 at a frequency in the vicinity of $f_2$. The vibrating system 15 fails to resonate when the contact surface 10 is not slipping. When the contact surface 10 begins to slip, on the other hand, the vibrating system 15 enters a resonant state in which the frequency component of the frequency $f_2$ strongly presents itself.

Further, in the case where the exciting force 16 contains both the frequency components in the vicinity of $f_1$ and $f_2$, the vibrating system 15 resonates regardless of whether the contact surface 10 is slipping or not. Nevertheless, the resonant frequency associated with the peak amplitude value undergoes a change.

Figure 10:
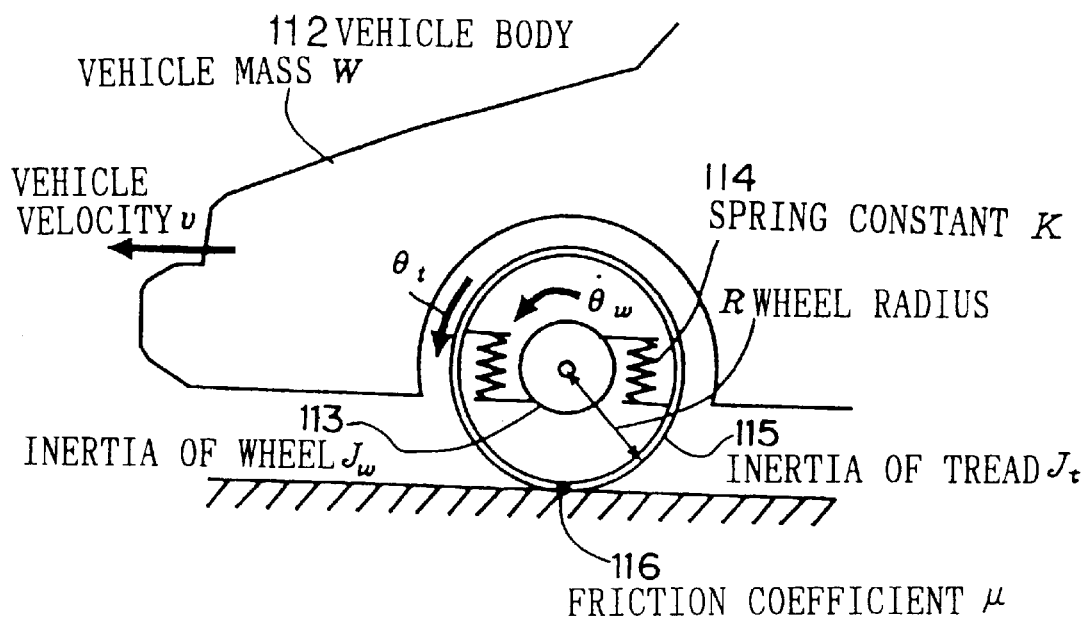
FIG. 10 is a diagram showing a dynamic model of the vehicle.

The above-mentioned model of the vibrating system in which an inertial member vibrates along a straight line can easily be applied extensively to a rotational vibrating system. A model of the rotational vibrating system, as shown in FIG. 10, comprises a vehicle body, a wheel and a road surface, representing the vibration phenomenon of the wheel in which a vehicle having the vehicle body 112 of weight W is running at a velocity V. The vibration phenomenon of this vibrating system will be explained below with reference to a model shown in FIG. 11 equivalently modeled with respect to the rotational axis of the wheel.

The braking force (regulating force) acts on the road surface through the surface of a tread 115 of the tire in contact with the road surface. This braking force is actually exerted on the vehicle body 112 as a reaction from the road surface. An equivalent model 117 of the vehicle weight as converted with respect to the rotational axis, therefore, is coupled to the other side of the wheel 113 through a friction element 116 between the tire tread and the road surface. This is analogous to the case in which the weight of the vehicle body can be simulated by a large inertia under the wheel, i.e., the mass opposite to the wheel as in a chassis dynamo unit.

Figure 11:
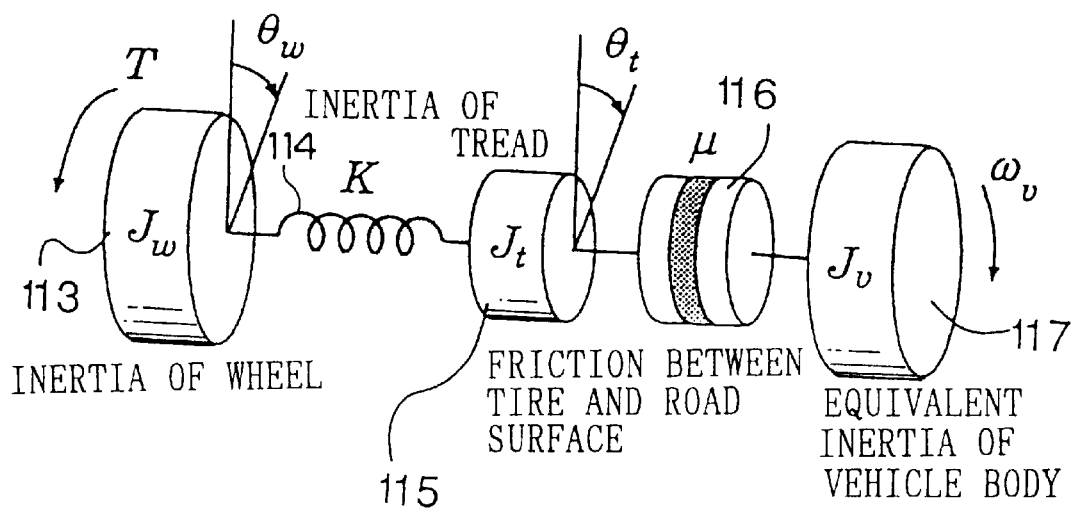
FIG. 11 is a diagram showing a dynamic model of a vehicle as converted with respect to the rotational axis thereof.

In FIGS. 10 and 11, the inertia moment of the wheel 113 including the tire rim is $J_w$, the spring constant of the spring element 114 between the rim and the tread 15 is K, the inertia of the tread 115 is $J_t$, the friction coefficient of the friction element 116 between the tread 115 and the road surface is $\mu$, and the inertia of the equivalent model 117 of the weight of the vehicle body 112 as converted with respect to the rotational axis is $J_v$. Then, the characteristics of the system as a whole are given by equations (5) to (7) below. The first-order differentiation d/dt with respect to time is hereafter denoted by ['] and the second-order differentiation $d^2/dt^2$ with respect to time denoted by ["].

$$J_w\theta_w'' = -T + K(\theta_t - \theta_w) \tag{5}$$

$$J_t\theta_t'' = -K(\theta_t - \theta_w) + \mu WR \tag{6}$$

$$J_v\omega_v' = -\mu WR \tag{7}$$

where $$w_w = \theta_w' \tag{8}$$

$$J_v = R^2 W \tag{9}$$

$$\omega_v = v/r \tag{10}$$

$\theta_w$ is the rotational angle of the wheel 113, $\theta_w''$ is the rotational angular acceleration of the wheel 113, $w_w$ is the rotational angular velocity of the wheel 113, $\theta_t$ is the rotational angle of the tread 115, $\theta_t''$ is the rotational angular acceleration of the tread 115, $\omega_v$ is the rotational angular velocity as converted with respect to the rotational axis of the vehicle body equivalent model 117, T is the braking torque applied to the wheel 113, W is the weight of the vehicle body, and R is the wheel radius. The braking torque T is actually obtained by controlling the pressure $P_b$ of the brake valve.

When the tire is gripping, the tread 115 and the vehicle equivalent model 117 are assumed to be directly coupled with each other. Then, the sum of the inertia of the vehicle equivalent model 117 and the inertia of the tread 115 resonates with the inertia of the wheel 113. Under this condition, the resonant frequency $f_1$ of the wheel resonant system is expressed as $$f_1 = \text{square root } \{(J_w + J_t + J_v)K/J_w(J_t + J_v)\}/2\pi \tag{11}$$

This assumes exactly the same form as equation (2). This condition corresponds to region A1 in FIG. 9.

Conversely, in the case where the friction coefficient $\mu$ of the tire approaches the peak $\mu$, it becomes difficult for the friction coefficient $\mu$ of the tire surface to change with respect to the slip ratio S, and the frequency component of the inertia of the tread 115 associated with the vibration ceases to affect the vehicle body equivalent model 117. In other words, the tread 115 and the vehicle body equivalent model 117 are equivalently separated from each other, so that the tread 115 resonates with the wheel 113. Under this condition, the resonant frequency $f_2$ of the wheel resonant system is given as $$f_2 = \text{square root } \{(J_w+J_t)K/J_wJ_t\}/2\pi \qquad (12)$$

This equation assumes exactly the same form as equation (4). This state corresponds to region A2 in FIG. 9, and generally, the tire is locked as the state transfers to region A3 the instant the peak $\mu$ is reached. The resonant gain of the wheel velocity for the resonant frequency, on the other hand, also is sharply reduced immediately before the peak The relative magnitude among the respective inertia is expressed as $$J_t < J_w < J_v \qquad (13)$$

This leads to $$f_1 < f_2 \qquad (14)$$

In other words, in the case where the tire comes to be locked, the resonant frequency of the wheel resonant system deviates toward a higher frequency. This change in the resonant frequency suddenly occurs in the vicinity of the peak $\mu$.

Even in the case where the model is simplified to such an extent as to ignore the inertia $J_t$ of the tread 115, a similar analysis is possible since the approach to the peak $\mu$ causes a change in the resonant gain of the wheel velocity and the resonant frequency of the wheel resonant system.

As described above, the resonant characteristics such as whether the vibrating system 15 or the wheel resonant system resonates or not, how the resonant frequency changes, which frequency component of the exciting force is amplified or attenuated with how much of resonant gain, depend on the friction characteristics of the contact surface. This is equivalent to say that if these resonant characteristics are detected, the friction characteristics of the contact surface (the state just about to slip, etc.) and the friction coefficient can be calculated.

(First embodiment)

An embodiment of the friction characteristics detecting apparatus utilizing the resonant characteristics will be described in detail below with reference to the accompanying drawings.

According to the first embodiment, a friction characteristics detecting apparatus of the present invention is applied to a load gripping apparatus like a crane for gripping and moving a load, for example, whereby the load can be gripped with proper force without damaging or dropping it. A load gripping apparatus according to the first embodiment is described with reference to FIGS. 1 and 2.

As shown in the front view of FIG. 1A, a load gripping apparatus according to this embodiment comprises a gripping means 22 for gripping the load 21, a gripping force generator 23 for applying the gripping force to the gripping means 22, a wire 24 attached on the gripping force generator 23 for lifting the whole weight, and a winch (not shown) for pulling the wire 24. The side external appearance of the load gripping apparatus is shown as in FIG. 1B, from which the gripping force 25 for gripping the load 21 is seen to be applied in the direction shown.

The maximum friction force generated on the contact surface between the gripping means 22 and the load 21 is determined by the product of the gripping force 25 and the static friction coefficient $\mu_{stat}$ on the contact surface. Accordingly, as long as the gripping force 25 is sufficiently large and the maximum friction force is more than the weight of the load 21, the load 21 does not slip down. As the gripping force decreases resulting in the maximum friction force decreasing below the weight of the load 21, in contrast, the load 21 slips down.

Figure 2:
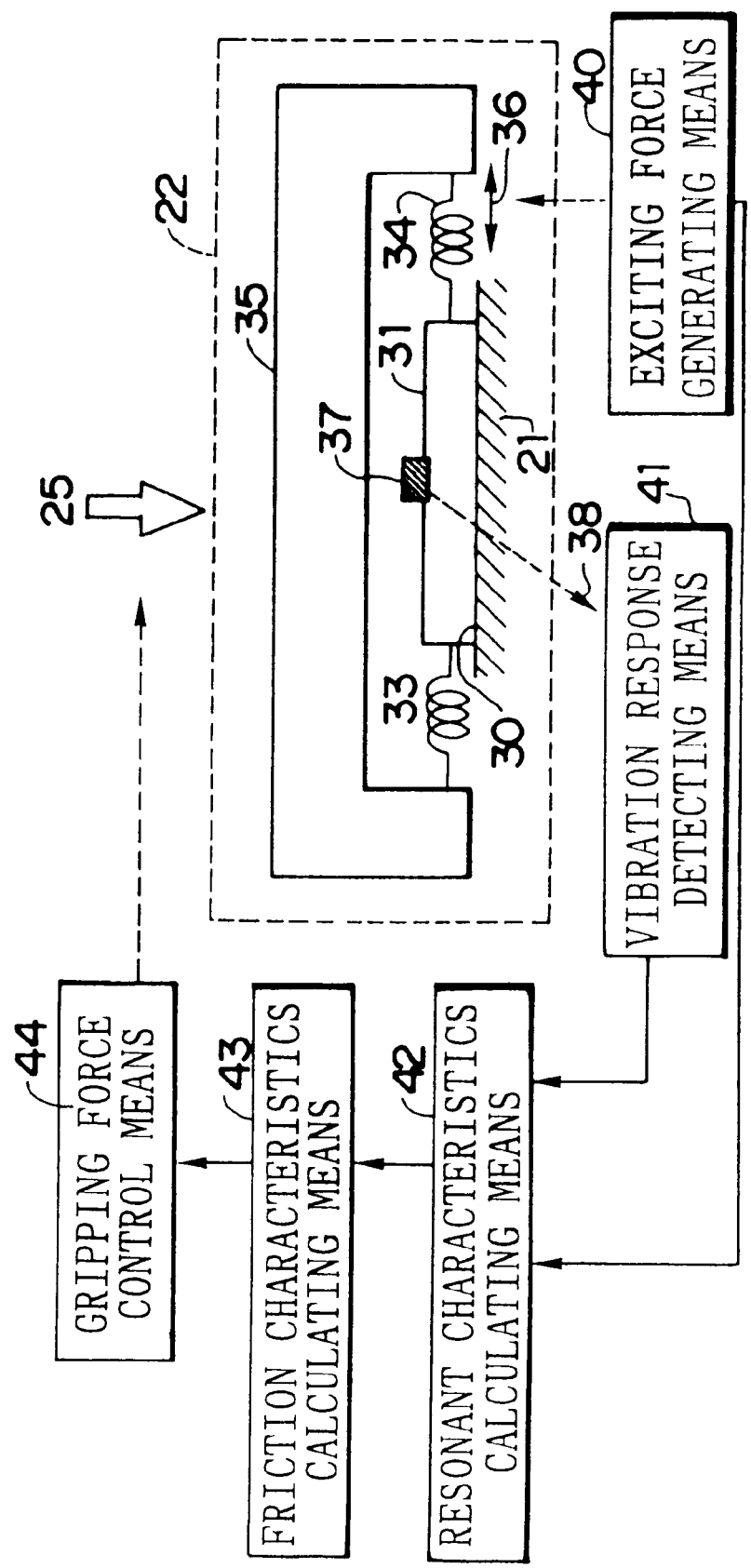
FIG. 2 is a block diagram showing the detailed configuration of the gripping means of the load gripping apparatus according to the first embodiment.

FIG. 2 shows a detailed configuration of the gripping means 22 and a control system for controlling the gripping force 25. As shown in FIG. 2, the gripping means 22 includes an inertial member 35 of mass $M_c$ making up an outer peripheral portion thereof, a contactor 31 of mass $M_a$ mounted on the side of the inertial member 35 in contact with the load 21 of mass $M_b$ through a spring element 33 and a spring element 34 each having a spring constant of K/2.

The contactor 31 is mounted in such a manner as to be displaced in horizontal direction through the spring element 33 and the spring element 34. More specifically, according to this embodiment, the direction of displacement of the spring elements is substantially parallel to the contact surface 30 and perpendicular to the direction in which the friction force is generated against the weight of the load 21.

A exciting force generating means 40 for causing a minor vibration of the contactor 31 by applying the exciting force 36 of a vibrating frequency $f_2$ (=square root $\{(M_a+M_c)K/M_aM_c\}/2\pi$) in the direction of displacing the spring element 33 and the spring element 34 is interposed between the contactor 31 and the inertial member 35. As shown in FIG. 1A, the exciting force 36 causes a minor vibration of the load 21 together with the contactor 31 in the horizontal direction 26. This exciting force generating means 40 can be readily realized by mounting a piezoelectric element, for example, on the mounting portion of the spring element 33 and the spring element 34 and displacing the piezoelectric element electrically. The exciting force generating means 40 can alternatively be easily realized by mounting a coil and a magnetic material on the contactor 31 and the inertial member 35 respectively and causing a minor vibration by a electromagnetic attraction and repulsion force.

Further, a vibration response detecting means 41 is mounted on the contactor 31 for detecting the response characteristics of the contactor 31 when a minor vibration is caused by the exciting force generating means 40. This response detecting means 41 can be realized by an accelerometer 37 for measuring the acceleration 38 of the contactor 31 under the exciting force 36, for example, as a response characteristic.

Also, a resonant characteristics calculating means 42 is provided for calculating the resonant characteristics of the gripping means 22 for gripping the load 21 on the basis of the response characteristics including the exciting force 36 applied by the exciting force generating means 40 and the acceleration 38 detected by the vibration response detecting means 41. The resonant characteristics are represented by, for example, the ratio of the amplitude of the vibration component of the acceleration 38 to the amplitude of the exciting force 36 (resonant gain) or the change in the resonant frequency.

The apparatus according to this embodiment further comprises a friction characteristics calculating means 43 for determining on the friction characteristics of the contact surface between the contactor 31 and the load 21 on the basis of the resonant characteristics calculated by the resonant characteristics calculating means 42, and a gripping force control means 44 for optimally braking the gripping force applied to the gripping means 22 by controlling the gripping force generating means 23 according to the friction characteristics determined on.

Now, the operation of the load gripping apparatus is described.

The vibration frequency $f_2$ of the exciting force applied by the exciting force generating means 40 is a resonant frequency of a vibrating system including the contactor 31, the spring element 33, the spring element 34 and the inertial member 35 with the contactor 31 out of contact with the load 21.

When the load 21 is securely gripped by the gripping force 25 of the gripping means 22, the load 21 vibrates completely following the minor vibration of the contactor 31 due to the exciting force 36. Under such a condition, therefore, the vibrating system is equivalent to a vibrating system with the mass $M_b$ of the load 21 added to the contactor 31 of mass $M_a$, so that the resonant frequency is $f_1$ (=square root $\{(M_a+M_b+M_c)K/(M_a+M_b)M_c\}/2\pi$). Consequently, as long as the load 21 remains securely gripped, the vibrating system is not resonated by the exciting force of the vibration frequency $f_2$, with the result that the acceleration 38 detected by the vibration response detecting means 41 and the resonant gain calculated by the resonant characteristics calculating means 42 assume small values as compared with the case in which the vibrating system otherwise resonates.

If the maximum friction force is reduced below a predetermined value at the contact surface 30 with the progressive reduction in the gripping force 25 of the gripping means 22, on the other hand, the load 21 is unable to follow the minor vibration of the contactor 31 under the exciting force 36. The resulting decrease in the effect of mass $M_b$ makes the resonant frequency of the vibrating system approach $f_2$. As a consequence, the frequency component of the frequency $f_2$ of the acceleration 38 detected by the vibration response detecting means 41 is amplified, whereby the resonant gain progressively increases. Especially immediately before the load 21 begins to slip, the vibration frequency component of acceleration suddenly increases.

After the resonant gain is calculated by the resonant characteristics calculating means 42, the friction characteristics calculating means 43 calculates the friction characteristics on the contact surface 30 on the basis of the resonant gain. In the case where the resonant gain is smaller than a reference value, for example, the friction characteristics associated with the non-slip condition are calculated, whereas in the case where the resonant gain is more than the reference value, the friction characteristics associated with the state immediately before slip begins are calculated. The values thus calculated representing the friction characteristics are used to discriminate and determine whether the contact surface 30 is not slipping, just about to slip or has begun to slip. According to this embodiment, the friction characteristics calculating means 43 may only determine whether the contact surface 30 is just about to slip or not.

The gripping force control means 44 controls the gripping force generating means 23 in such a manner as to maintain the gripping force 25 at a required minimum value on the basis of the calculation of the friction characteristics. More specifically, in the case where the contact surface 30 is not slipping, the load 21 is securely gripped, and therefore the gripping force generating means 23 is controlled so as to reduce the gripping force 25, while when the determination on the friction characteristics is that the contact surface 30 is just about to slip, the gripping force 25 is increased. If the resonant characteristics such as the resonant gain calculated by the resonant characteristics calculating means 42 are transmitted to the gripping force control means 44, the gripping force 25 can be controlled directly on the basis of the value of the resonant characteristics. In such a case, the need of the friction characteristics calculating means 43 is eliminated.

As described above, the friction characteristics can be continuously and accurately detected, and therefore the gripping force can be controlled to a minimum value required immediately before the load begins to slip. Hence, damage in the load due to an unnecessarily large gripping force can be avoided. Also, since the fact is utilized that the resonant frequency of the vibrating system is subject to a considerable variation depending on the friction characteristics, the detection sensitivity is very high and is not easily affected by a disturbance. Further, the control system can be configured at low cost in a simplified fashion with a high reliability.

(Second embodiment)

The principle of detecting the friction characteristics using the resonant characteristics can be applied also to a friction coefficient measuring system for measuring the friction coefficient. Such an application is described below with reference to a friction coefficient measuring system according to a second embodiment shown in FIGS. 3 and 4.

Figure 3A:
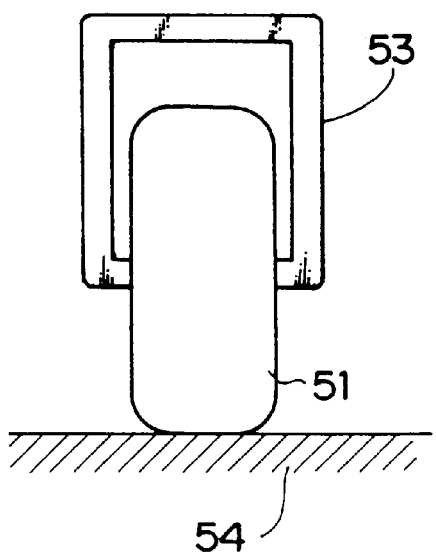

As shown in the front view of FIG. 3A, the friction coefficient measuring system comprises a tire 51 kept in contact with the surface to be measured 54 (road surface) by the weight of the measuring system, a mounting stay 53 for supporting the tire 51 and a control system not shown. The mounting stay 53 is mounted on a device such as a vehicle body (not shown) which utilizes the friction coefficient measured by the measuring system. Hereafter, the mounting stay 53 is assumed to be mounted on a vehicle body.

Figure 3B:
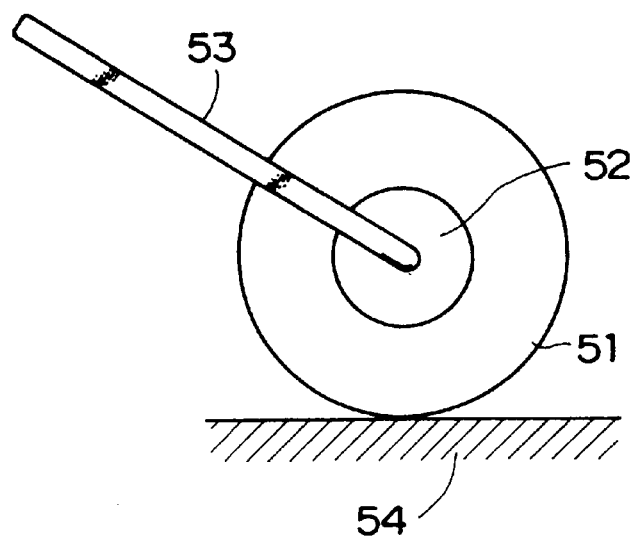

It is also seen from the side view of FIG. 3B that a wheel motor 52 for rotating the tire is arranged on the side of the wheel.

Figure 4:
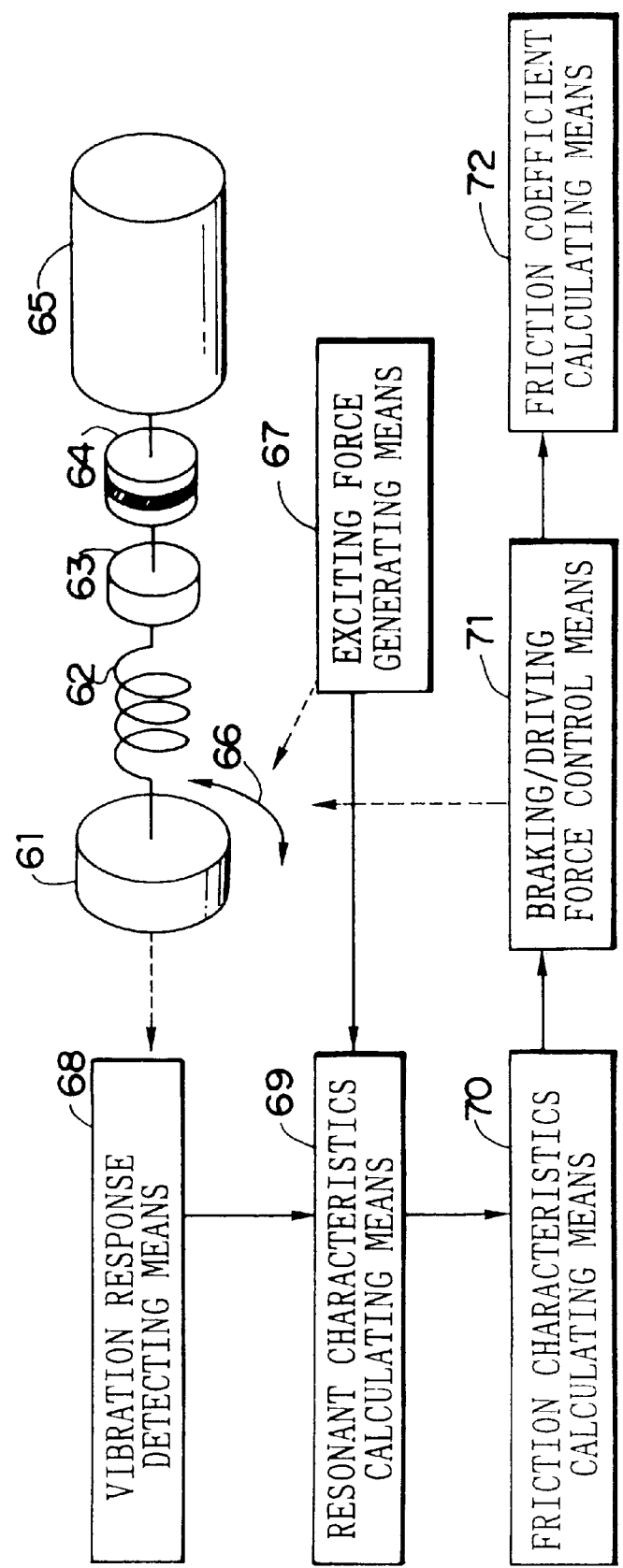
FIG. 4 is a block diagram showing a configuration and a model of a friction coefficient measuring system as converted around the rotational axis thereof according to the second embodiment.

The general configuration of the control system of the friction coefficient measuring system configured as shown in FIGS. 3A and 3B and an equivalent model of the vibrating system including the measuring system, the surface to be measured 54 and the vehicle body is shown in FIG. 4.

According to FIG. 4, the control system of the friction coefficient measuring system shown in FIGS. 3A and 3B includes a exciting force generating means 67 for superposing the minor frequency component of the resonant frequency $f_1$ (=square root $(K/M_c)/2\pi$) on the torque command for the wheel motor 52 of inertial moment $M_c$, a resonant characteristics calculating means 69 for calculating the resonant characteristics by detecting the frequency component of the rotational speed of the wheel motor 52 superposed with the minor frequency component, a friction characteristics calculating means 70 for determining the friction characteristics between the surface to be measured 54 and the tire 51 on the basis of the resonant characteristics detected, a braking/exciting force control means 71 for controlling the braking/exciting force exerted on the wheel motor 52 at a maximum level on the basis of the friction characteristics determined, and a friction coefficient calculating means 72 for measuring the static friction coefficient of the contact surface by dividing the braking/exciting force by the weight of the measuring system.

Each element of the equivalent model of the vibrating system shown in FIG. 4 is equivalent to each of the following elements shown in FIGS. 3A and 3B respectively. The inertial member 61 corresponds to the rotor of the wheel motor 52 of inertial moment $M_c$, the spring element 62 corresponds to the torsion spring of spring constant K of the side wall of the tire 51, and the inertial member 63 corresponds to the belt portion of the tire 51 of inertial moment $M_a$. Also, the contact surface 64 corresponds to the contact surface between the tire 51 and the surface to be measured 54. The inertial member 65 is such that the inertia of the stator of the wheel motor 52, the mounting stay 53 and the vehicle body on which the present measuring system is mounted is expressed as an equivalent inertial moment $M_b$ on the same axis. The resonant characteristics dependent on the friction characteristics of the contact surface 64 in the equivalent model shown in FIG. 4 follows exactly the same principle as the equivalent model shown in FIG. 11 and therefore will not be described in detail.

Now, the operation of a friction coefficient measuring system according to this embodiment will be explained with reference to the equivalent model shown in FIG. 4.

First, suppose that a tire 51 is rolling without slip on a surface to be measured 54. In this case, a vibrating system including the measuring system, the surface to be measured 54 and the vehicle body is approximated as a double inertial system including an inertial moment $(M_a+M_b)$ and an inertial moment $M_c$ with a resonant frequency $f_1$ (=square root $\{(M_a+M_b+M_c)K/(M_a+M_b)M_c\}/2\pi$), which, considering $(M_a+M_b)>>M_c$, can be approximated as $f_1$=square root $(K/M_c)/2\pi$ A exciting force generating means 67 superposes a minor frequency component of a frequency $f_1$ (square root $(K/M_c)/2\pi$) on a torque command to a wheel motor 52. As a result, a vibrating torque 66 for vibrating at a frequency $f_1$ is exerted on an inertial member 61 equivalent to the rotor of the wheel motor 52. When the contact surface is not slipping, the resonant frequency $f_1$ of this vibrating system coincides with the frequency of the vibrating torque, and therefore the vibrating system resonates.

Next, a vibration response detecting means 68 detects the frequency component of the rotational speed of the inertial member 61 generated by the vibrating torque 66. In the case where the contact surface is not slipping as described above, a large rotational speed frequency component of the resonant frequency $f_1$ is detected by the vibration response detecting means 68.

Then, a resonance characteristics calculating means 69 calculates the amplitude value of the frequency component of the resonant frequency $f_1$ as a resonant characteristic. This is effective in the case where the amplitude of the vibrating torque 66 always assumes a constant value. An alternative is, as in the first embodiment, is to determine the ratio (resonant gain) of the amplitude of the frequency component of the rotational speed to the amplitude of the vibrating torque 66.

A friction characteristics calculating means 70 calculates the friction characteristics of the contact surface on the basis of the resonant characteristics. When the amplitude value is larger than a reference value, for example, the friction characteristics of the contact surface not slipping are calculated, while when the amplitude value is smaller than the reference value, the friction characteristics with the contact surface having begun to slip are calculated. In this case, a large rotational speed frequency component appears, and therefore it is determined that the contact surface is not slipping on the basis of the calculated friction characteristics.

In the next step, a braking/exciting force control means 71 controls the braking/exciting force acting on the surface to be measured 54 through the tire 51 on the basis of the calculated friction characteristics in such a manner that the contact surface assumes the friction characteristics just about to slip. In other words, in the case where the system is mounted on a vehicle body or the like running at a predetermined velocity, a braking force for suppressing the rotation of the tire 51 is applied. When the system is mounted on an apparatus without any exciting force or standing alone, on the other hand, the exciting force is applied from the wheel motor 52 for rotating the tire 51. A large load may be imposed on the measuring system in advance so that with the increase in the exciting force, the friction force against the exciting force immediately may increase up to a maximum friction force.

As described above, in the case where the contact surface is determined not to be slipping, the braking/exciting force control means 71 controls the braking/exciting force to increase. As a result, the friction force is increased in resistance to the braking/exciting force.

Figure 5:
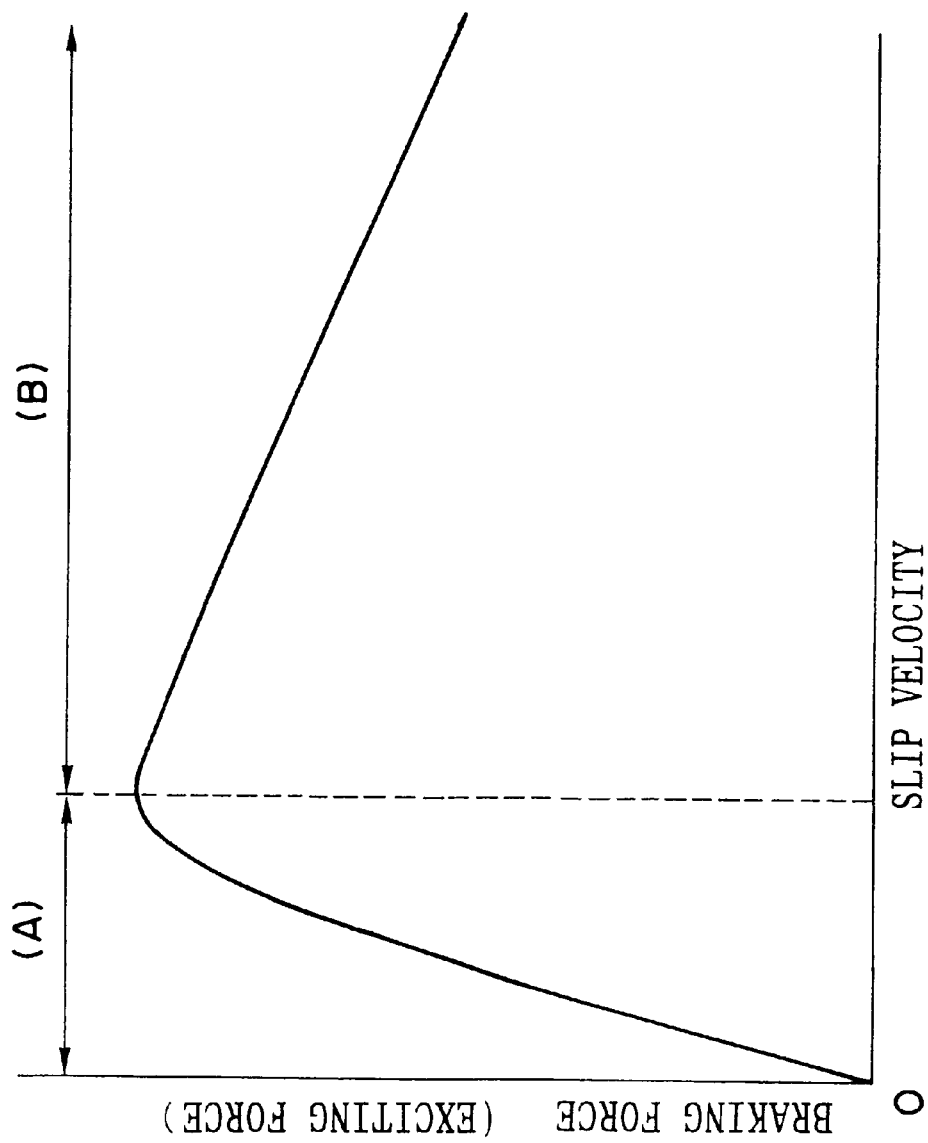
FIG. 5 is a diagram showing the characteristics of the ratio between braking force and exciting force versus the slip velocity.

The relation of the braking/exciting force versus the slip velocity (relative speed between the tread of the tire 51 and the surface to be measured 54) is shown in FIG. 5. In FIG. 5, the range of the slip velocity in region A corresponds to the state in which the contact surface 64 is not slipping. It is seen that the braking/exciting force increases with the slip velocity in region A. The reason why the slip velocity assumes a value more than zero in region A where the contact surface should not be slipping is that the tread of the tire 51 is elastically deformed before the tread leaves the ground after it lands on the ground. During this period, the contact surface 64, which is not actually slipping, appears as if it is slipping in terms of the relation between the vehicle body velocity and the rotational speed of the tire 51.

In the case where it is determined that the contact surface is not slipping as described above, the braking/exciting force continues to increase, but when this force exceeds a maximum friction force, the contact surface 64 actually begins to slip. In FIG. 5, the region B after the braking/exciting force reaches the peak value corresponds to the state in which the contact surface 64 actually begins to slip.

As the contact surface begins to slip, the inertial member 65 can no longer follow the vibration of frequency $f_1$, and the effect of the inertial moment $M_c$ thereof is reduced. This vibrating system thus is approximated as a double inertial system including the inertial moment $M_a$ and the inertial moment $M_c$, with the resonant frequency of $f_2$ (=square root $\{(M_a+M_c)K/M_aM_c\}/2\pi$). Hence, the vibrating system fails to resonate even when the exciting force generating means 67 is subjected to minor vibration with the vibrating torque 66 of frequency $f_1$, and the frequency component of the rotational speed detected by the vibration response detecting means 68 is reduced. When the amplitude calculated by the resonant characteristics calculating means 69 is reduced below a reference value, the friction characteristics calculating means 70 calculates the friction characteristics of the contact surface in slip state. On the basis of this friction characteristics, the braking/exciting force control means 71 controls the braking/exciting force to decrease the same. In the example of FIG. 5, the braking/exciting force is seen to decrease with the increase in slip velocity in region B.

As will be understood from the foregoing description, when determination is made that the contact surface 64 is not slipping, the braking/exciting force is controlled to increase the same, while when it is determined that the contact surface 64 is slipping, the braking/exciting force is controlled to decrease the same. In this way, the friction characteristics of the contact surface are maintained in a state just about to slip. In other words, the value of force exerted on the tire tread by the braking/exciting force is kept at a value in the vicinity of the maximum friction force of the contact surface 64.

The friction coefficient calculating means 72 divides the braking/exciting force held to secure the maximum friction force by the weight of the friction coefficient measuring system thereby to measure the static friction coefficient of the contact surface 64. As a consequence, the static friction coefficient can be easily measured in the case where the friction coefficient of the contact surface 64 undergoes a continuous change.

Figure 6B:
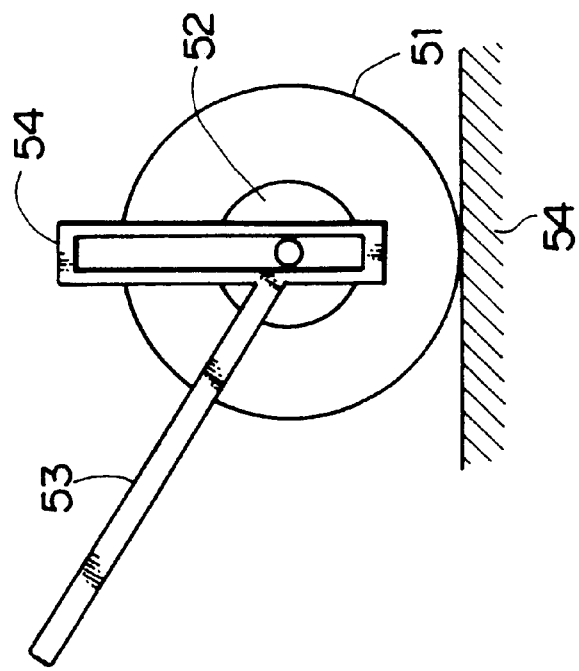
Figure 6A:
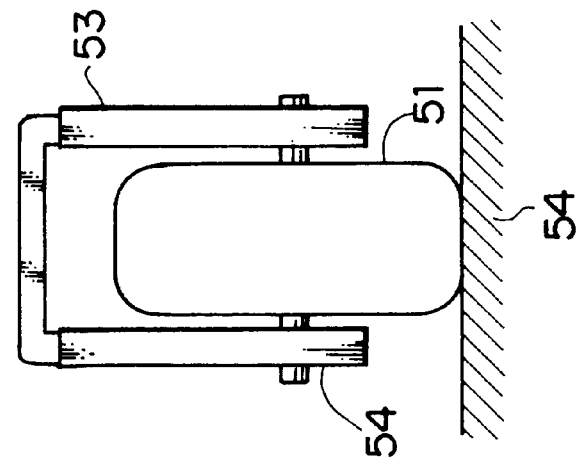
Figure 7:
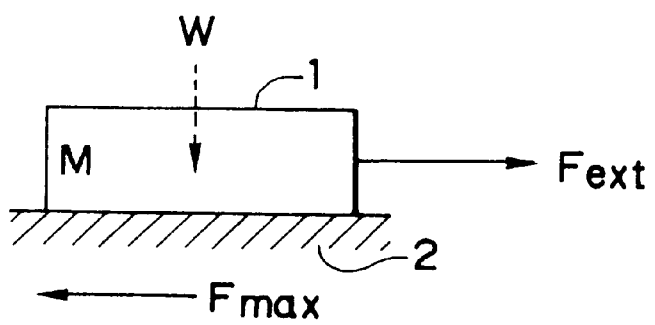
FIG. 7 is a diagram showing the relation between external force and maximum friction force.

In the case where the surface to be measured 54 is rough like a road surface, for example, an extraneous vertical force may be imposed on the surface to be measured 54 in addition to the weight of the measuring system or the surface to be measured 54 fails to contact the measuring system, resulting in a considerable calculation error of the friction coefficient. As a measure against this inconvenience, a mounting stay 54 may be provided to enable the rotational center axis of the tire 51 to move vertically as shown in FIGS. 6A and 6B. This provision permits the friction measuring system according to this embodiment to contact the surface to be measured 54 by its own weight even in the presence of some roughness, and thereby to measure the friction coefficient accurately. In this case, the weight of the measuring system providing the divisor of the maximum friction force is equal to the total load of the component parts of the wheel motor 52 and the tire 51 except for the load including the mounting stay 53.

The friction coefficient measuring system according to this embodiment can be used alone. When it is mounted as the fifth wheel of the vehicle through the mounting stay 53, however, an application to the control of the vehicle is also possible. In such a case, it is necessary that the friction coefficient between the tire 51 and the road surface is equal to the friction coefficient between the tire of the vehicle on which it is mounted and the road surface, or the two friction coefficients are previously known in a predetermined relation.

In an application to a power steering unit, for example, whenever the turning characteristics (lateral acceleration) is determined to be in a critical condition on the basis of the friction coefficient of the road surface and the lateral acceleration, the steering power of the power steering system is controlled at a magnitude different from the normal value. As a result of this control operation, the friction coefficient can be measured accurately by the friction coefficient measuring system even in the presence of many disturbances with an ever-changing friction coefficient of the road surface, thereby leading to an accurate and steady determination on the critical condition of turning characteristics for an improved safety.

Another application finds in the anti-lock braking control. In this case, on the vehicle body side, the maximum friction force between the tire and the road surface is calculated on the basis of the friction coefficient measured by the friction coefficient measuring system, and the braking force is controlled in such a manner that the force exerted between the tire and the road surface is equal to the maximum friction force calculated. Alternatively, the friction coefficient calculated by this system is not directly delivered, but the friction characteristics calculated by the friction characteristics calculating means 70 is delivered to a vehicle body controller, and the braking force is controlled in such a manner that the detected friction characteristics represent a state just about to slip. In the latter case, the tire 51 of the friction coefficient measuring system is required to be regulated into the same friction characteristics as the tire on the vehicle body.

The invention is not limited to the above-mentioned embodiments thereof. Although the exciting force generating means is used to cause a minor vibration in an inertial member at the resonant frequency of a vibrating system in both the first and second embodiments, the exciting force generating means may not be used depending on the field of application.

According to the first embodiment in which an external force having the frequency characteristics such as of white noise is applied as a disturbance continuously, for example, the effective value of the full frequency components and the effective value of the resonant frequency component are determined from the frequency component detected, and the resonant characteristics can be detected on the basis of the ratio between these effective values.

According to the second embodiment, on the other hand, in which an impulse-like or stepwise external force is applied frequently, the resonant frequency component and the other frequency components (or the full frequency components) are separated from the response waveform of this input, so that the resonant characteristics can be determined from the ratio between these components.

As seen from above, the first and second embodiments, which use no exciting force generating means, have a simple configuration advantageous not only in terms of reliability but also economy.

Although the amplitude value of the vibrating system and the resonant gain are calculated as resonant characteristics according to the embodiments described above, the vibrating system may be resonated with a exciting force containing all the resonant frequencies of the vibrating system corresponding to respective friction characteristics thereby to calculate the change in resonant frequency at the maximum amplitude.

Further, the frequency of the exciting force may not exactly coincide with the resonant frequency, but may assume a frequency value in the vicinity of the resonant frequency as far as the resonant characteristics of the vibrating system can be positively identified.

(Third embodiment)

Explanation will be made about the principle of a friction characteristics detecting apparatus according to a third embodiment.

Specifically, with the increase in the braking force up to the state where the wheel is locked, the resonant characteristics change in the vicinity of the peak value of the braking force of the road surface, and the resonant gain for the resonant frequency is reduced to have a smaller value as compared with the one at the time of gripping. Suppose a reference gain is set to a sufficiently small value and the average braking force is controlled in such a manner that the resonant gain detected coincides with the reference gain. The braking force then can be held at a value in the vicinity of the peak value, and the friction characteristics of the road surface can be detected on the basis of the relative magnitude of the braking force.

Figure 12:
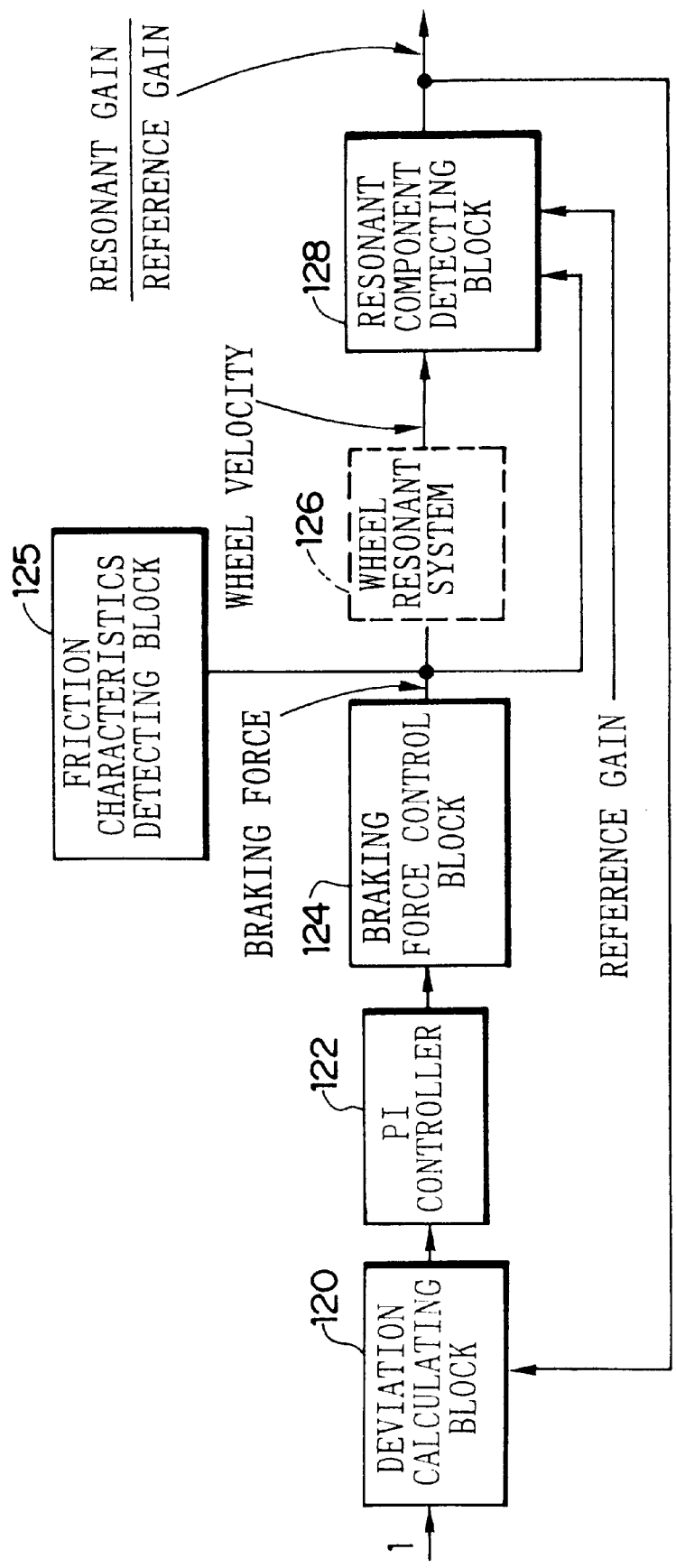
FIG. 12 is a diagram showing the configuration of a friction characteristic detecting apparatus according to a third embodiment.

The configuration of a friction characteristics detecting apparatus according to the third embodiment is schematically shown in FIG. 12.

As shown in FIG. 12, this friction characteristics detecting apparatus comprises a deviation calculating block 120 for calculating the deviation between the ratio of the resonant gain to the reference gain produced from the apparatus and unity, a PI controller 122 for calculating a control signal for making the deviation calculated by the deviation calculation means coincide with zero, a braking force control system 124 for applying the braking force (braking pressure on the wheel) to the wheel resonant system 126 (FIGS. 10 and 11) including the road surface, the vehicle body and the wheel in accordance with the control signal calculated by the PI controller 122, a resonant component detecting block 128 for producing the ratio between the resonant gain and the reference gain on the basis of the braking force, the reference gain and the wheel velocity detected, and a friction characteristics detecting block 125 for detecting the friction characteristics of the road surface on the basis of the relative magnitude of the braking force exerted on the wheel by the braking force control system 124.

The output terminal of the resonant component detecting block 128 is connected with the input terminal of the deviation calculating block 120. Also, the wheel resonant system 126 includes a wheel velocity detection sensor not shown. This sensor applies the detected wheel velocity to the resonant component detecting block 128.

Figure 13:
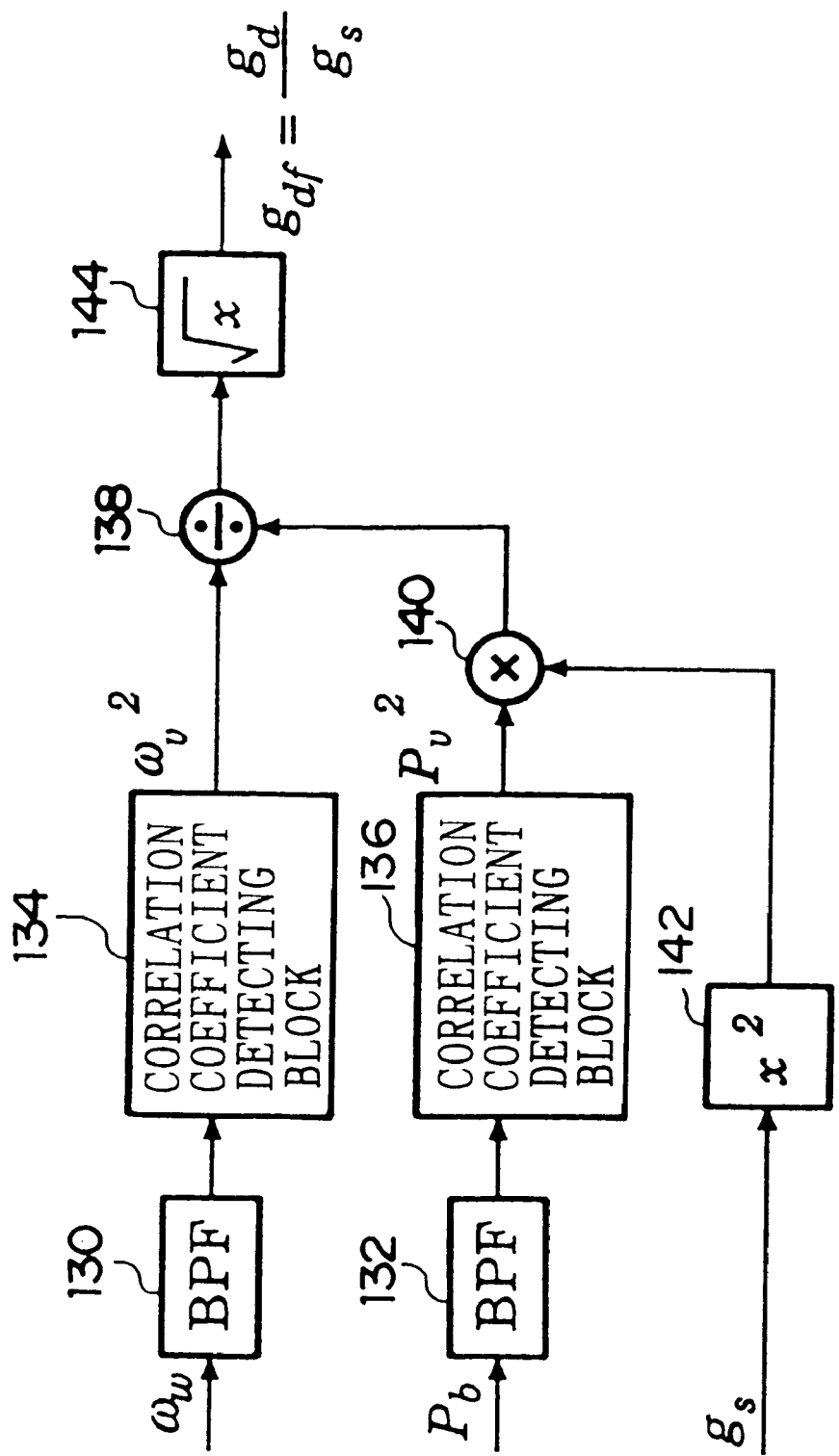
FIG. 13 is a diagram showing the configuration of a resonant component detector according to the third embodiment.

Now, a detailed configuration of the resonant component detecting block 128 is shown in FIG. 13. The resonant component detecting block 128 is configured for detecting a predetermined frequency component. In the case where a detection signal is read into a computer through an AD converter, for example, a frequency component of 41.7 Hz providing 12 sample points per half period is detected on the assumption that the operation sampling time of the computer is 1 ms.

As shown in FIG. 13, the resonant component detecting block is configured to be supplied with a wheel velocity $\omega_w$, a braking force $P_b$ from the braking force control system 124 to the wheel resonant system 126 and a reference gain $g_s$.

The input terminal (not shown) supplied with the wheel velocity $\omega_w$ is connected with a correlation coefficient detecting block 134 through a BPF (bandpass filter) for removing the noise components and the DC component. This correlation coefficient detecting block 134 calculates the power $\omega_v^2$ of a predetermined frequency component of the wheel velocity $\omega_w$. $\omega_v$ designates an amplitude value of the particular frequency component of the wheel resonant system 126.

Also, the input terminal (not shown) supplied with the braking force $P_b$ as a braking pressure to the wheel is connected with a correlation coefficient detecting block 136 through a BPF 132 for removing the DC component and the noise components. This correlation coefficient detecting block 136 calculates the power $P_v^2$ of a predetermined frequency component of the braking force $P_b$. $P_v$ provides an amplitude value of the particular frequency component of the braking force.

The input terminal (not shown) supplied with the reference gain $g_s$ is connected to a square-root means 142 for calculating the square of the input signal. The square-root means 142 is connected to one of the input terminals of a multiplier 140 for multiplying the two input signals with each other. In other words, one of the input terminals of the multiplier 140 is supplied with $g_s^2$.

The other input terminal of the multiplier 140 is connected with the output terminal of the correlation coefficient detecting block 136 and is input with $P_v^2$. As a result, the multiplier 140 produces $g_s^2 N P_v^2$.

The output terminals of the correlation coefficient detecting block 134 and the multiplier 140 are connected with a divider 138 for dividing one of the two input signals by the other and determining the ratio therebetween. In this connection arrangement, the divider 138 outputs $\omega_v^2/(P_v^2 g_s^2) = g_d^2/g_s^2$, where the resonant gain $g_d = \omega_v/P_v$.

What is actually wanted to be detected is the ratio $g_{df}$ of the resonant gain to the reference gain. The output terminal of the divider 138, therefore, is connected to the square root calculating block 144 for calculating the square root of the input value. This square root calculating block 144 outputs $g_{df} = g_d/g_s$, which constitutes an output of the resonant component detecting block 128.

A means for calculating the square root alternative to the square root calculating block 144 is provided by a program routine created for the particular purpose. Actually, however, this is difficult for the reason of the control period. Instead, means is preferable for interpolating the value with reference to a square root table prepared in advance. Taking the whole control system into consideration, the condition to be achieved by the control operation is the one in which the resonant gain $g_d$ assumes a value in the vicinity of the reference gain $g_s$. This indicates the fact that $g_{df} = g_d/g_s$ is substantially near to unity. The square $g_{df}^2$ of this value, therefore, exists in the substantial vicinity of unity. In the configuration of FIG. 13, $g_{df}^2$ is calculated by dividing $g_d^2$ of power dimension by the reference gain $g_s^2$ before calculating the square root, and a value substantially in the vicinity of unity is used as an input value to the square root calculating means 144. As a consequence, once a table is prepared by which the square root of a value in the vicinity of unity can be referred to as a square root table of the square root calculating means 144, the square root value can be obtained with a small capacity and with rapidity.

Assuming that the time length of the time sequence data is $T_1$, the minimum frequency of the frequency spectrum obtained is given as $1/T_1$ (Hz), thereby making it possible to obtain a frequency component equal to an integer multiple of $1/T_1$. Using the data at 48 sampling points with the sampling time of the control system as 1 ms, the minimum frequency is about 20.8 Hz and the second component about 41.7 Hz. The correlation coefficient detecting blocks 134 and 136 are configured as shown in FIG. 14 in order to calculate the power of the 41.7 Hz component.

Figure 14:
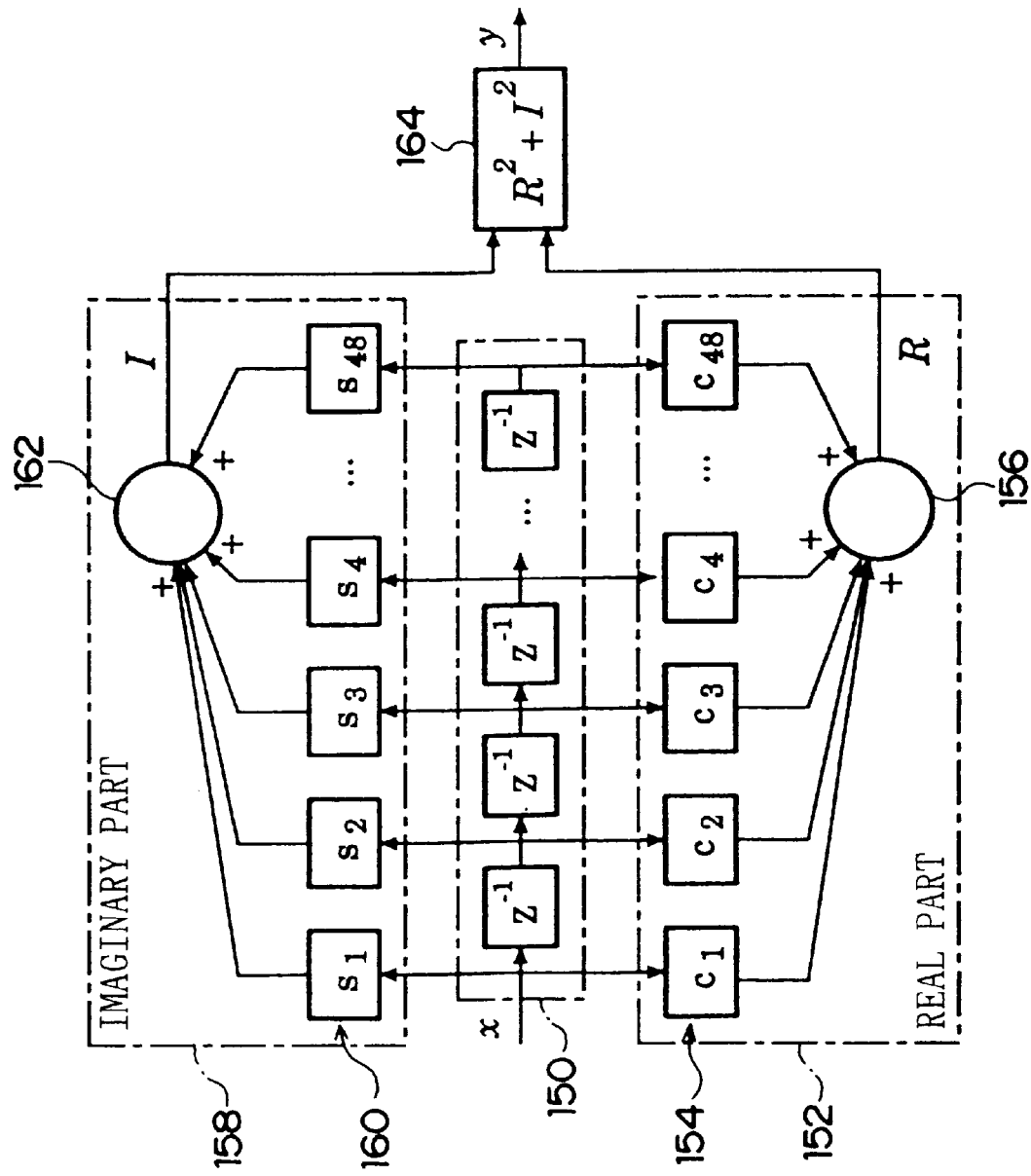
FIG. 14 is a diagram showing the configuration of a correlation coefficient detector according to the third embodiment.

As seen from FIG. 14, the correlation coefficient detecting block includes a delay circuit 150 for delaying and outputting the time sequence data $\{x_1, x_2, \ldots x_n\}$ of the input signal x having a predetermined time length at intervals of one sample, a real part calculating means 152 for calculating the real number R of the Fourier coefficient of the time sequence data, an imaginary part calculating means 158 for calculating the imaginary number I of the Fourier coefficient, and an output means 164 for calculating the sum of the square of R and I, $R^2 + I^2$.

The delay circuit 150 includes a plurality of unit delay elements $z^{-1}$ connected in series for delaying the time sequence data by one sample each. The number of the unit delay elements $z^{-1}$ is coincident with the number 48 of the samples of the time sequence data. An output signal line is provided for sending each sample data to the real part calculating means 152 and the imaginary part calculating means 158 before the time sequence data are applied to the respective unit delay elements $z^{-1}$.

These output signal lines are connected respectively to the coefficient multiplier 154 of the real part calculating means 152 and the coefficient multiplier 160 of the imaginary part calculating means 158. The coefficient multiplier 154 multiplies the sample data $x_1, x_2, \ldots, x_{48}$ by coefficients $c_1, c_2, \ldots, c_{48}$ respectively, and the coefficient multiplier 160 is adapted to multiply the sample data $x_1, x_2, \ldots x_{48}$ by coefficients $s_1, s_2, \ldots s_{48}$ respectively.

The output terminal of the coefficient multiplier 154 is connected to an adder 156, which produces an output R as the sum of all the products. The output terminal of the coefficient multiplier 160, in contrast, is connected to an adder 162 for producing the sum of all the products as I.

More specifically, R and I are given as $$R = \sum_{i=1}^{48} c_i x^i \qquad (13)$$

-continued $$I = \sum_{i=1}^{48} S_i x^i$$

Taking the coefficients $c_i$ and $s_i$ $$Si = \frac{1}{24} \sin\left\{\frac{\pi}{24}(2i-1)\right\} \quad (i = 1, 2, \ldots, 48), \tag{14}$$

$$Ci = \frac{1}{24} \cos\left\{\frac{\pi}{24}(2i-1)\right\} \quad (i = 1, 2, \ldots, 48)$$

Then, R and I are nothing but the real number and imaginary number of the Fourier coefficient for the 41.7 Hz frequency component.

The adders 156 and 162 are connected to an output means 164 for producing the sum of the square of R and I, $y = R^2 + I^2$. Consequently, the power value of the component of frequency 41.7 Hz is obtained.

Now, description will be made about the operation of a friction characteristics detecting apparatus according to the third embodiment.

The resonant component detecting block 128 calculates the ratio $g_{df}$ of the resonant gain to the reference gain of the wheel resonant system 126 on the basis of the wheel velocity $\omega_w$ detected, the braking force $P_b$ and the reference gain $g_s$ input. The deviation calculating block 120 calculates the deviation between $g_{df}$ and unity and applies the deviation to the PI controller 122. The PI controller 122 applies a control signal for making the calculated difference coincide with zero to the braking force control system 124. The braking force control system 124 controls the braking force of the wheel resonant system 126 on the basis of the control signal. The friction characteristics detecting block 125 detects the road surface friction characteristics on the basis of relative magnitude of the braking force.

More specifically, when $g_{df}$ is larger than unity, it is determined that the braking force is sufficiently small as compared with the peak value of friction force between the tire and road surface, in which case the braking force is increased to approach the peak value. In the vicinity of the peak value of the braking force, by contrast, the resonant characteristics change with the resonant gain reduced to have a smaller values as compared with the one at the time of gripping. It is therefore determined that the state in which $g_{df}$ is smaller than unity is one which the peak value is being approached. In such a case, the braking force is reduced in such a manner as to prevent further increase of the braking force. When the braking force is controlled in order for $g_{df}$ to approach unity in this way, a braking force is realized in a condition where the friction force is sufficiently in the vicinity of the peak value, and the friction characteristics between tire and road surface can be accurately detected from the value of the particular braking force.

(Fourth embodiment)

First, explanation will be made about the principle of a friction characteristics detecting apparatus according to a fourth embodiment. The fourth embodiment comprises the resonant component detecting block 128 configured in a more simplified way.

In a resonant system including the vehicle body, the tire and the road surface shown in FIG. 11, as already described, the resonant frequency $f_g$ of the system with the tire surface gripping the road surface is given as $$f_g = \frac{1}{2\pi} \text{square root}\left\{\frac{J_w + J_t + J_v}{J_w(J_t + J_v)}K\right\} \tag{15}$$

The ratio of the minor amplitude of the wheel velocity to the minor amplitude of the braking force (braking pressure) under this condition is expressed as $$G_d = jA + \alpha B \text{ (j: imaginary number unit)} \tag{16}$$

where $$J_A = J_t + J_v + J_w \quad J_B = J_t + J_v \tag{17}$$

$$A = \frac{J_v(J_B J_t - J_v J_w)K \text{ square root }(J_A J_B J_w K)}{J_A J_v^2 J_w^2 K^2} \tag{18}$$

$$B = \frac{J_B^3 J_w K R^2 W}{J_A J_v^2 J_w^2 K^2} \tag{19}$$

where $\alpha$ is a slope of the tire-road surface friction coefficient $\mu$ to the slip velocity $\Delta\omega = \omega_v - \omega_w$. In other words, if each parameter for an actual vehicle is known, the phase characteristics thereof can also be determined in advance. If the phase $\theta_d$ of equation (16) is known, the single sinusoidal wave for obtaining the correlationship can be implemented only with a single component indicated by $$cs_i = \frac{1}{24} \sin\left\{\frac{\pi}{24}(2i-1) + \theta_d\right\} \quad (i = 1, 2, \ldots, 48) \tag{20}$$

Thus, the amplitude of the resonant component can be obtained simply with the calculation $$y = \sum_{i=1}^{48} cs_i x_i \tag{21}$$

In this case, it is possible to selectively extract the frequency component correlated with the excitation of the braking pressure. Only the resonant characteristics of the vibrating system including the vehicle body, the wheel and the road surface can thus be selectively detected substantially free of the effect of vibration noises of the road surface. Generally, the value A in equation (16) is so small that the phase difference assumes a value of zero or in the vicinity of $\pi$ radians. When the wheel approaches a locked state, the phase difference drifts. Since only the phase component associated with the gripping is observed, however, the rate at which the resonant gain decreases increases, thereby further improving the detection sensitivity.

Figure 16:
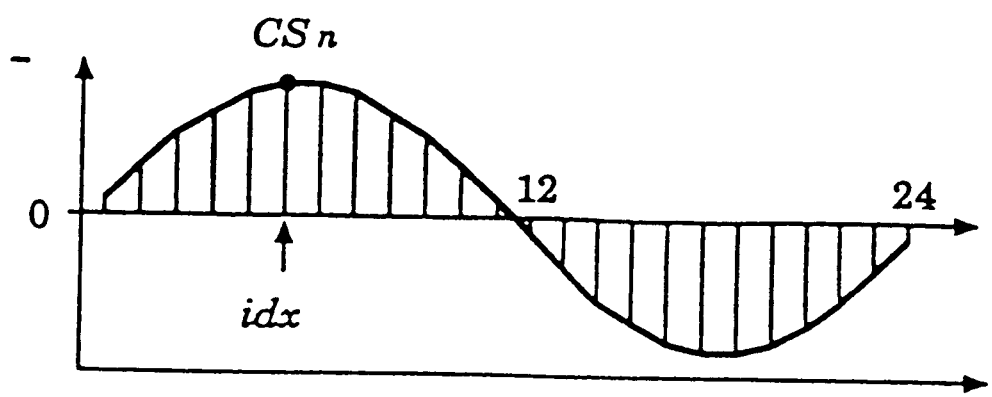
FIG. 16 is a diagram showing a waveform of a single sinusoidal wave correlated with an input signal according to the fourth embodiment.

FIG. 16 shows a graph of a single sinusoidal wave of equation (20) for obtaining a correlationship. As shown in FIG. 16, the sample idx of an input signal x increases monotonically from 1 to 24 sample by sample in step with the exciting force (braking force) applied to the object, and is reset to sample 1 after sample 24. The initial value associated with $z^{-48}$ assumes zero, and if the time point of the first 48th sample is designated as j, from equation (21), $y^j$ is given as $$y_j = \sum_{i=1}^{48} cs_i^j x_i^j \qquad (22)$$

where $cs_i^j$, $x_i^j$ are the numbers attached to the data at the past 48 points as of time j from the past values of 1 to 48. The value $y^{j+1}$ at the next sampling time point j+1 is given as $$y^{j+1} = \sum_{i=1}^{48} cs_i^{j+1} x_i^{j+1} \qquad (23)$$

Obviously, $$cs^{j+1}{}_i = cs^j{}_{i+1}, \; x^{j+1}{}_i = x^j{}_{i+1} \qquad (24)$$

From the periodicity of $cs_i^j$, the following equation is finally obtained.

$$y^{j+1} = y^j + cs^{j+1}{}_{48}(x^{j+1}{}_{48} - x^j{}_i) \qquad (25)$$

$cs^{j+1}{}_{48}$ represents the very value of $CS_n$ at time point j+1, $x^{j+1}{}_{48}$ the latest value of x at time point j+1, and $x^J{}_1$ the value 48 samples before at time point j+1. Thus the resonant component detecting block can be configured in the way shown in FIG. 15.

Figure 15:
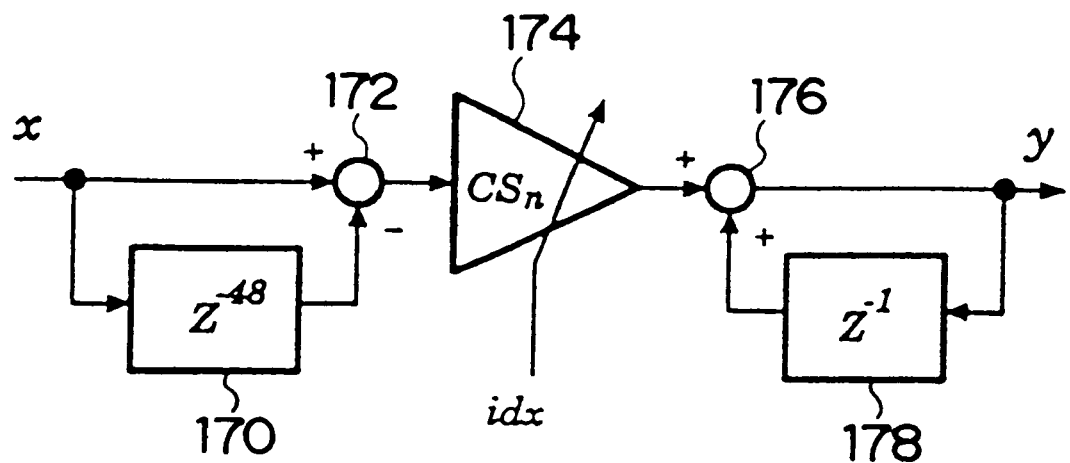
FIG. 15 is a diagram showing the configuration of a resonant component detector according to a fourth embodiment.

As shown in FIG. 15, this friction characteristics detecting apparatus comprises a delay element 170 for determining the signal value $x^{-48}$ 48 samples before the input signal x, a difference calculating means 172 for determining the difference between the input signal x and $x^{-48}$, calculating means 174 for calculating $CS_n$ for idx, a delay element 178 for determining the signal value $y^{-1}$ one sample before the output y, and an adding means 176 for calculating the sum of the outputs of the calculating means 174 and the delay element 178. This apparatus thus can calculate the result of equation (25).

According to this configuration, the calculation quantity is only two summations and one multiplication for each sample, thereby making it possible to simplify the processing and increase the speed thereof as compared with the third embodiment.

(Fifth embodiment)

The principle of a friction characteristics detecting apparatus according to a fifth embodiment will be described. The configuration of this embodiment is similar to that of the third or fourth embodiment, and therefore will not be described in detail.

According to the fifth embodiment, the calculation result of the deviation calculating block 120, i.e., the input A to the PI controller 122 is obtained by subtracting unity from the reciprocal of $g_{df}$ as shown below.

$$\Delta = 1 - \frac{1}{g_{df}} \qquad (26)$$

The value obtained simply by subtracting $g_{df}$ from unity can be used also as a deviation A as according to the third embodiment. In this case, however, the braking force assumes a value sufficiently near to the peak value when $g_{df}$ is smaller than unity, often leading to a locked state in response to only a slight change in braking force. From the viewpoint of controllability, the equation (26) in which the sensitivity increases with the decrease in $g_{df}$ below unity should preferably be used as an input.

By applying the value $\Delta$ of equation (26) to the PI controller 122, the value $\Delta$ sharply increases progressively as the ratio between resonant gain and reference gain approaches to a value smaller than unity, i.e., a locked state. In other words, an increased sensitivity permits an even more accurate detection of the friction characteristics by holding the braking force at a peak value while avoiding the possibility of falling in a locked state.

The present invention is not confined to the above-mentioned cases representing embodiments. The PI controller according to the third to fifth embodiments, for example, can be replaced by a robust controller such as what is called a double-freedom controller or H∞ controller of a higher performance. In such a case, the braking force controller increases or decreases the average braking force in accordance with the output of the PI controller, while at the same time exciting the wheel resonant system by the resonant frequency.

The result of operation for detecting the friction characteristics of an actual road surface will be explained below with reference to a friction characteristics detecting apparatus according to an embodiment of the invention.

Figure 9:
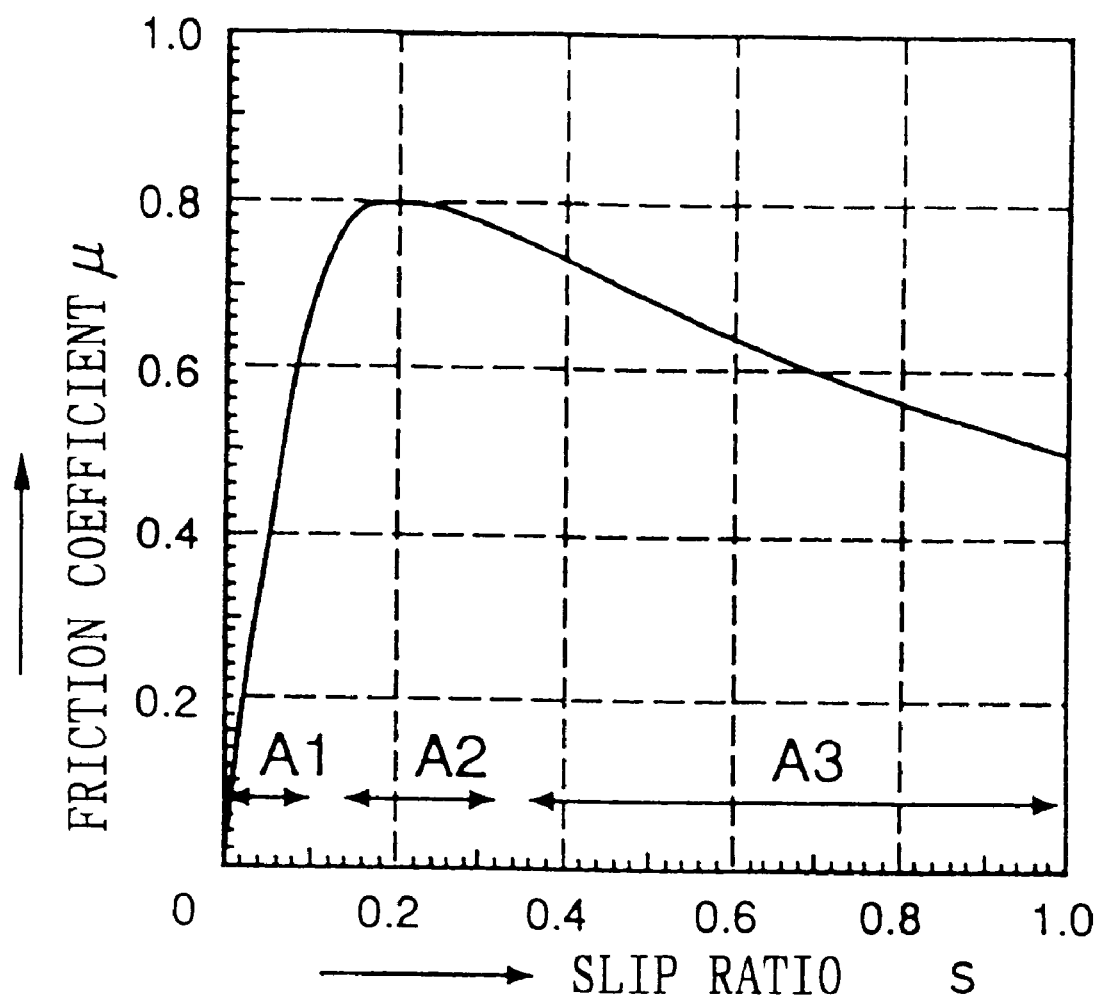
FIG. 9 is a diagram showing the characteristics of the friction coefficient $\mu$ between tire and road surface versus the slip ratio S.

As already described, the relation between road surface friction coefficient $\mu$ and slip ratio S exhibits a characteristic as shown in FIG. 9. In this $\mu$–S characteristic curve, the friction coefficient $\mu$ assumes a peak value at a certain slip ratio (in region A2 in FIG. 9).

Figure 17A:
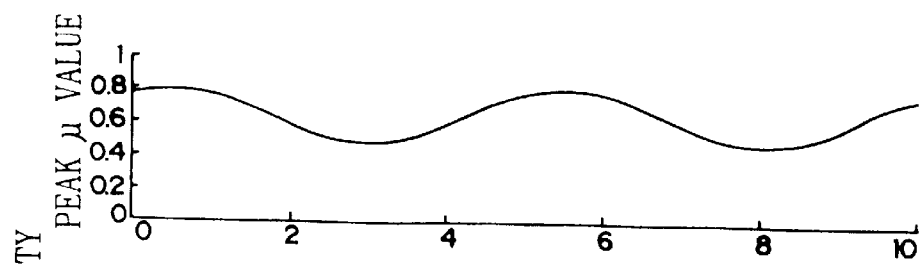
Figure 17B:
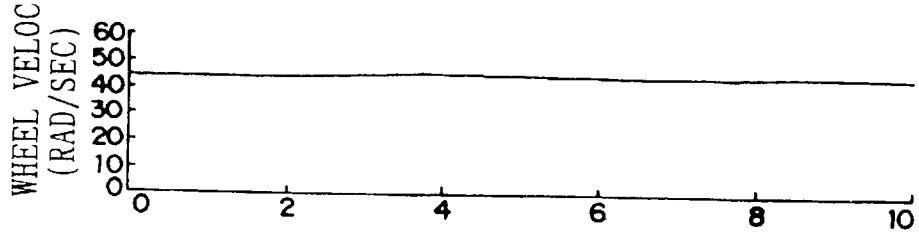
Figure 17C:
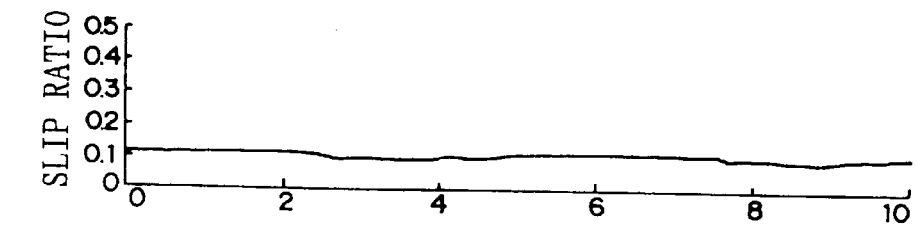

As shown in FIG. 17A, time waveforms of the wheel velocity in rad/s, the slip ratio, the road surface friction coefficient estimated by the friction characteristics detecting apparatus, the resonant gain in rad/s/Nm and the control force (control torque in Nm) applied to the wheels under this condition in the case where the peak value of $\mu$ undergoes a sinusoidal change in the range of 0.5 to 0.8 are shown in FIGS. 17B to 17F respectively.

Figure 17D:
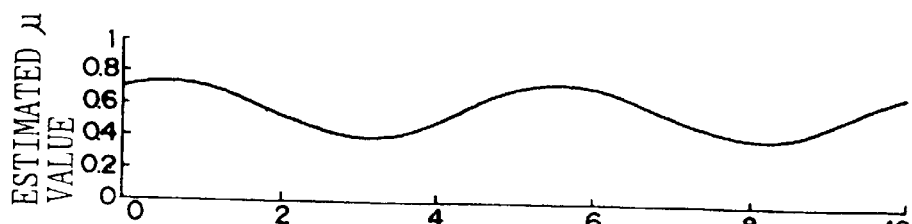
Figure 17E:
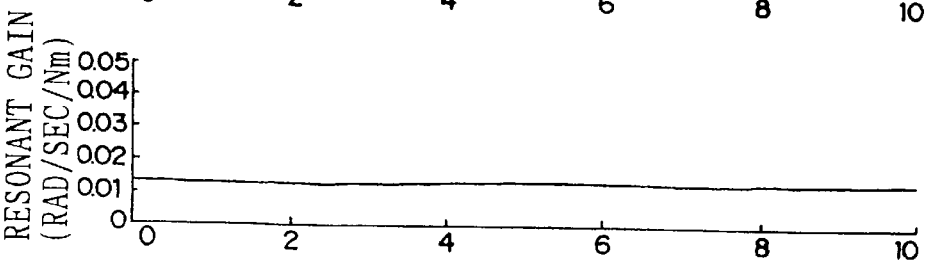
Figure 17F:
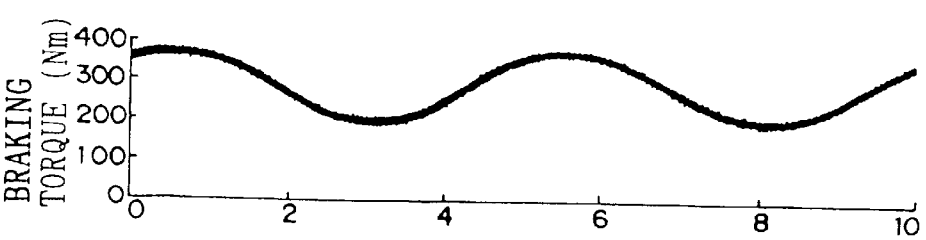

FIG. 17E shows that the resonant gain detected is held substantially at 0.013 rad/s/Nm and at the gain value for the peak value of the braking force. The change in braking force under this condition, as shown in FIG. 17F, well reflects the characteristics of the friction coefficient of the road surface. Also, as shown in FIG. 17D, the estimated value of the friction coefficient of the road surface determined from this value of braking force is near to the peak value of the friction coefficient of the actual road surface.

Figure 18A:
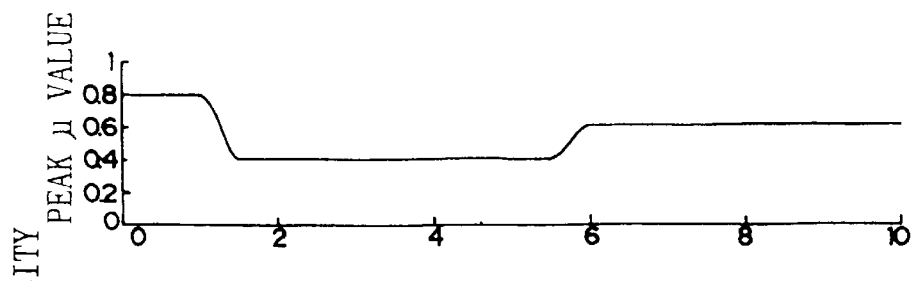

FIGS. 18B to 18F show time waveforms of the wheel velocity in rad/s, the slip ratio, the friction coefficient of the road surface estimated by the friction characteristics detecting apparatus under consideration, the resonant gain in rad/s/Nm and the control force (control torque in Nm) acting on the wheels in the case where the peak value of $\mu$ undergoes a stepwise change in the range of 0.4 to 0.8 as shown in FIG. 18A.

Figure 18B:
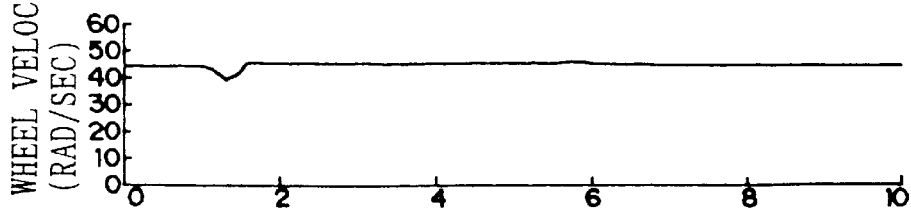
Figure 18C:
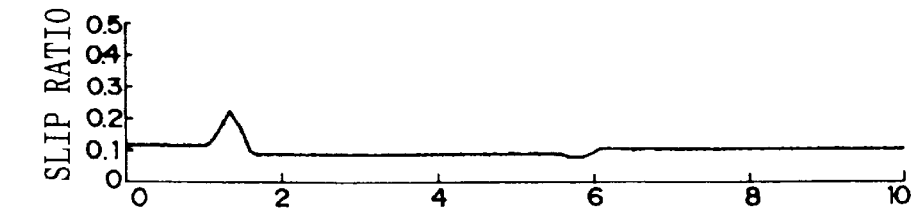
Figure 18D:
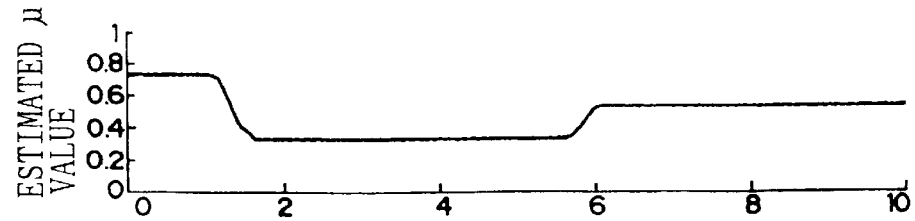
Figure 18E:
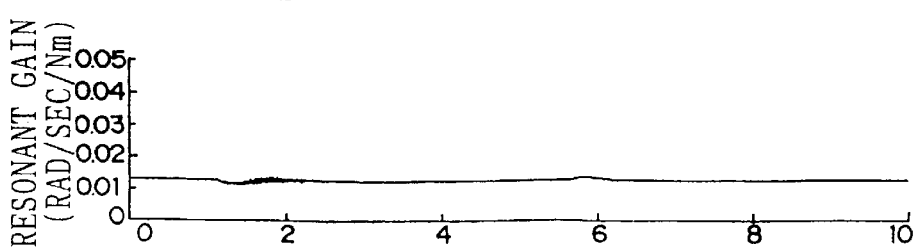
Figure 18F:
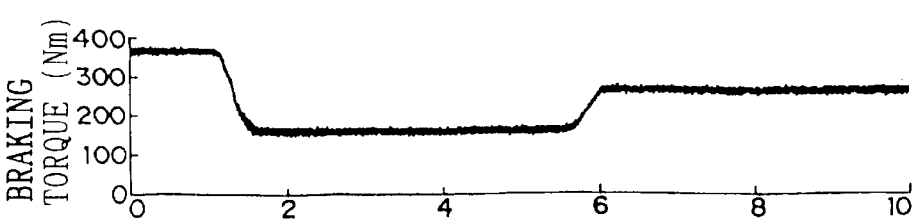

It is found from FIG. 18E that the resonant gain detected is held at about 0.013 rad/s/Nm or at the gain value associated with the peak value of the braking force. When the road surface friction coefficient $\mu$ is decreased in steps, the slip ratio sharply increases to such an extent that the wheel instantaneously presents a locking tendency (FIGS. 18B and 18C). A stable state, however, is restored afterwards. This change in the braking force well reflects the characteristics of the road surface friction coefficient as shown in FIG. 18F. Further, FIG. 18D indicates that the estimated value of the road surface friction coefficient determined from this braking force assumes a value near to the peak value of the friction coefficient for the actual road surface.

It is seen from these results of operation that the road surface friction coefficient determined from the value of the braking force can be accurately obtained by the friction characteristics detecting apparatus according to the present invention.

What is claimed is:

1. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element;

exciting force generating means for generating an exciting force containing selected one of the resonant frequency of said vibrating system and the frequency component in the vicinity of said resonant frequency and exciting said vibrating system by said exciting force;

vibration response detecting means for detecting the quantity of state of the vibration response of said vibrating system excited by said exciting force generating means;

resonant characteristics calculating means for calculating the resonant characteristics of said vibrating system on the basis of the quantity of state of the exciting force generated by said exciting force generating means and the quantity of state of the vibration response detected by said vibration response detecting means; and friction characteristics calculation means for calculating the friction characteristics of the contact surface on the basis of the resonant characteristics calculated by said resonant characteristics calculating means.

2. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element, said vibrating system being excited by an external force;

external force detecting means for detecting the quantity of state of said external force;

vibration response detecting means for detecting the quantity of state of the vibration response of said vibrating system excited by said external force;

resonant characteristics calculating means for calculating the resonant characteristics of said vibrating system on the basis of the quantity of state of said external force detected by said external force detecting means and the quantity of state of the vibration response detected by said vibration response detecting means; and friction characteristics calculating means for calculating the friction characteristics of the contact surface on the basis of the resonant characteristics calculated by said resonant characteristics calculating means.

3. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element;

exciting means for exciting said vibrating system in the direction of generation of the friction force by the exciting force containing selected one of the resonant frequency of said vibrating system and the frequency component in the vicinity of said resonant frequency;

vibration response detecting means for detecting the quantity of state of the vibration response of said vibrating system excited by said exciting means;

resonant characteristics calculating means for calculating the resonant characteristics of said vibrating system on the basis of the quantity of state of the exciting force generated by said exciting means and the quantity of state of the vibration response detected by said vibration response detecting means;

operating force generating means for generating and exerting the operating force on said contact surface;

maximum friction force control means for controlling said operating force on the basis of the resonant characteristics calculated by said resonant characteristics calculating means in such a manner that said contact surface assumes a state just about to slip; and friction characteristics calculation means for calculating the friction characteristics of the contact surface on the basis of the maximum friction force of the maximum friction force control means.

4. An apparatus according to claim 3, further comprising:

maximum friction force calculating means for calculating the value of maximum friction force of the contact surface on the basis of the operating force associated with the state of said contact surface just about to slip realized by said maximum friction force control means; and friction coefficient calculating means for calculating the friction coefficient of said contact surface on the basis of the value of the maximum friction force calculated by said maximum friction force calculating means.

5. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element, said vibrating system being excited by an external force;

external force detecting means for detecting the quantity of state of said external force;

vibration response detecting means for detecting the quantity of state of the vibration response of said vibrating system excited by said external force;

resonant characteristics calculating means for calculating the resonant characteristics of said vibrating system on the basis of the quantity of state of the external force detected by said external force detecting means and the quantity of state of the vibration response detected by said vibration response detecting means;

operating force generating means for generating and exerting an operating force on said contact surface;

maximum friction force control means for controlling said operating force on the basis of the resonant characteristics calculated by said resonant characteristics calculating means in such a manner that said contact surface assumes a state just about to slip; and friction characteristics calculation means for calculating the friction characteristics of the contact surface on the basis of the maximum friction force of the maximum friction force control means.

6. An apparatus according to claim 5, further comprising:

maximum friction force calculating means for calculating the value of maximum friction force of the contact surface on the basis of the operating force associated with the state of said contact surface just about to slip realized by said maximum friction force control means; and friction coefficient calculating means for calculating the friction coefficient of said contact surface on the basis of the value of the maximum friction force calculated by said maximum friction force calculating means.

7. A method for detecting friction characteristics comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element;

generating an exciting force containing selected one of the resonant frequency of said vibrating system and the frequency component in the vicinity of said resonant frequency and exciting said vibrating system by said exciting force;

detecting the quantity of state of the vibration response of said vibrating system excited by said exciting force generating step;

calculating the resonant characteristics of said vibrating system on the basis of the quantity of state of the exciting force generated by said exciting force generating step and the quantity of state of the vibration response detected by said vibration response detecting step; and calculating the friction characteristics of the contact surface on the basis of the resonant characteristics calculated by said resonant characteristics calculating step.

8. A method for detecting friction characteristics comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element, and said vibrating system being excited by an external force;

detecting the quantity of state of said external force;

detecting the quantity of state of the vibration response of said vibrating system excited by said external force;

calculating the resonant characteristics of said vibrating system on the basis of the quantity of state of said external force detected by said external force detecting step and the quantity of state of the vibration response detected by said vibration response detecting step; and calculating the friction characteristics of the contact surface on the basis of the resonant characteristics calculated by said resonant characteristics calculating step.

9. A method for detecting friction characteristics comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element;

exciting said vibrating system in the direction of generation of the friction force by the exciting force containing selected one of the resonant frequency of said vibrating system and the frequency component in the vicinity of said resonant frequency;

detecting the quantity of state of the vibration response of said vibrating system excited by said exciting step;

calculating the resonant characteristics of said vibrating system on the basis of the quantity of state of the exciting force generated by said exciting step and the quantity of state of the vibration response detected by said vibration response detecting step;

generating and exerting an operating force on said contact surface;

controlling said operating force on the basis of the resonant characteristics calculated by said resonant characteristics calculating step in such a manner that said contact surface assumes a state just about to slip; and calculating the friction characteristics of the contact surface on the basis of the maximum friction force of the maximum friction force control step.

10. A method according to claim 9, further comprising the steps of:

calculating the value of maximum friction force of the contact surface on the basis of the operating force associated with the state of said contact surface just about to slip realized by said operation force control step; and calculating the friction coefficient of said contact surface on the basis of the value of the maximum friction force calculated by said maximum friction force calculating step.

11. A method for detecting friction characteristics comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element, and said vibrating system being excited by an external force;

detecting the quantity of state of said external force;

detecting the quantity of state of the vibration response of said vibrating system excited by said external force;

calculating the resonant characteristics of said vibrating system on the basis of the quantity of state of the external force detected by said external force detecting step and the quantity of state of the vibration response detected by said vibration response detecting step;

generating and exerting an operating force on said contact surface;

controlling said operating force on the basis of the resonant characteristics calculated by said resonant characteristics calculating step in such a manner that said contact surface assumes a state just about to slip; and calculating the friction characteristics of the contact surface on the basis of the maximum friction force of the maximum friction force control step.

12. A method according to claim 11, further comprising the steps of:

calculating the value of maximum friction force of the contact surface on the basis of the operating force associated with the state of said contact surface just about to slip realized by said operation force control step; and calculating the friction coefficient of said contact surface on the basis of the value of the maximum friction force calculated by said maximum friction force calculating step.

13. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element;

exciting means for exciting said vibrating system in the direction of generation of the friction force by the exciting force containing selected one of the resonant frequency of said vibrating system and the frequency component in the vicinity of said resonant frequency;

vibration response detecting means for detecting the quantity of state of the vibration response of said vibrating system excited by said exciting means;

resonant characteristics calculating means for calculating the resonant characteristics of said vibrating system on the basis of the quantity of state of the exciting force generated by said exciting means and the quantity of state of the vibration response detected by said vibration response detecting means;

operating force generating means for generating and exerting the operating force on said contact surface;

maximum friction force control means for controlling said operating force on the basis of the resonant characteristics calculated by said resonant characteristics calculating means in such a manner that said contact surface assumes a state just about to slip;

maximum friction force calculating means for calculating the value of maximum friction force of the contact surface on the basis of the operating force associated with the state of said contact surface just about to slip realized by said maximum friction force control means; and friction coefficient calculating means for calculating the friction coefficient of said contact surface on the basis of the value of the maximum friction force calculated by said maximum friction force calculating means.

14. An apparatus for detecting friction characteristics comprising:

a vibrating system including an element on one side of a contact surface generating a friction force, a spring element connected to said element and adapted to be displaced in the direction substantially parallel to said contact surface and an inertial member connected to the other end of said spring element, said vibrating system being excited by an external force;

external force detecting means for detecting the quantity of state of said external force;

vibration response detecting means for detecting the quantity of state of the vibration response of said vibrating system excited by said external force;

resonant characteristics calculating means for calculating the resonant characteristics of said vibrating system on the basis of the quantity of state of the external force detected by said external force detecting means and the quantity of state of the vibration response detected by said vibration response detecting means;

operating force generating means for generating and exerting an operating force on said contact surface;

maximum friction force control means for controlling said operating force on the basis of the resonant characteristics calculated by said resonant characteristics calculating means in such a manner that said contact surface assumes a state just about to slip;

maximum friction force calculating means for calculating the value of maximum friction force of the contact surface on the basis of the operating force associated with the state of said contact surface just about to slip realized by said maximum friction force control means; and friction coefficient calculating means for calculating the friction coefficient of said contact surface on the basis of the value of the maximum friction force calculated by said maximum friction force calculating means.

15. A method for detecting friction characteristics, comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element;

exciting said vibrating system in the direction of generation of the friction force by the exciting force containing a selected one of the resonant frequency of said vibrating system and the frequency component in the vicinity of said resonant frequency;

detecting the quantity of state of the vibration response of said vibrating system excited by said exciting step;

calculating the resonant characteristics of said vibrating system on the basis of the quantity of state of the exciting force generated by said exciting step and the quantity of state of the vibration response detected by said vibration response detecting step;

generating and exerting an operating force on said contact surface;

controlling said operating force on the basis of the resonant characteristics calculated by said resonant characteristics calculating step in such a manner that said contact surface assumes a state just about to slip;

calculating the value of maximum friction force of the contact surface on the basis of the operating force associated with the state of said contact surface just about to slip realized by said operation force control step; and calculating the friction coefficient of said contact surface on the basis of the value of the maximum friction.

16. A method for detecting friction characteristics, comprising the steps of:

forming a vibrating system, said vibrating system including an element on one side of a contact surface generating a friction force, a spring element connected to said element and adapted to be displaced in the direction substantially parallel to said contact surface and an inertial member connected to the other end of said spring element, and said vibrating system being excited by an external force;

detecting the quantity of state of said external force;

detecting the quantity of state of the vibration response of said vibrating system excited by said external force;

calculating the resonant characteristics of said vibrating system on the basis of the quantity of state of the external force detected by said external force detecting step and the quantity of state of the vibration response detected by said vibration response detecting step;

generating and exerting an operating force on said contact surface;

controlling said operating force on the basis of the resonant characteristics calculated by said resonant characteristics calculating step in such a manner that said contact surface assumes a state just about to slip;

calculating the value of maximum friction force of the contact surface on the basis of the operating force associated with the state of said contact surface just about to slip realized by said operation force control step; and calculating the friction coefficient of said contact surface on the basis of the value of the maximum friction force calculated by said maximum friction force calculating step.

* * * * *